US011092599B2

(12) United States Patent
Hanson et al.

(10) Patent No.: US 11,092,599 B2
(45) Date of Patent: Aug. 17, 2021

(54) BIOSENSOR FOR DETECTING SMELL, SCENT, AND TASTE

(71) Applicant: Aromyx Corporation, Palo Alto, CA (US)

(72) Inventors: Chris Hanson, Sunnyvale, CA (US); William Harries, Redwood City, CA (US); Victor Todd Cushman, Wilmington, DE (US); Ed Costello, Pleasanton, CA (US)

(73) Assignee: Aromyx Corporation, Mountain View, CA (US)

( * ) Notice: Subject to any disclaimer, the term of this patent is extended or adjusted under 35 U.S.C. 154(b) by 0 days.

(21) Appl. No.: 15/441,062

(22) Filed: Feb. 23, 2017

(65) Prior Publication Data
US 2017/0242004 A1 Aug. 24, 2017

Related U.S. Application Data

(60) Provisional application No. 62/299,005, filed on Feb. 24, 2016.

(51) Int. Cl.
G01N 33/566 (2006.01)
G01N 33/569 (2006.01)
G01N 21/77 (2006.01)
G01N 33/554 (2006.01)

(52) U.S. Cl.
CPC ........... *G01N 33/566* (2013.01); *G01N 21/77* (2013.01); *G01N 33/554* (2013.01); *G01N 33/56961* (2013.01); *G01N 2333/726* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,482,835 A | 1/1996 | King et al. |
| 5,739,029 A | 4/1998 | King et al. |
| 5,789,184 A | 8/1998 | Fowlkes |
| 5,876,951 A | 3/1999 | Fowlkes et al. |
| 6,001,553 A | 12/1999 | Broach et al. |
| 6,100,042 A | 8/2000 | Fowlkes et al. |
| 6,159,705 A | 12/2000 | Trueheart et al. |
| 6,168,927 B1 | 1/2001 | King et al. |
| 6,251,605 B1 | 6/2001 | Ostanin et al. |
| 6,255,059 B1 | 7/2001 | Klein et al. |
| 6,325,475 B1 | 12/2001 | Hayes et al. |
| 6,355,473 B1 | 3/2002 | Ostanin et al. |
| 6,504,008 B1 | 1/2003 | Xu et al. |
| 6,555,325 B1 | 4/2003 | Oehlen |
| 6,855,550 B2 | 2/2005 | King et al. |
| 6,864,060 B1 | 3/2005 | Fowlkes et al. |
| 7,022,513 B2 | 4/2006 | Xu et al. |
| 7,081,360 B2 | 7/2006 | Nadkarni et al. |
| 7,090,991 B2 | 8/2006 | Oehlen |
| 7,105,309 B2 | 9/2006 | Fowlkes et al. |
| 7,122,305 B2 | 10/2006 | Klein et al. |
| 7,223,533 B2 | 5/2007 | Ostanin et al. |
| 7,223,550 B2* | 5/2007 | Dhanasekaran ..... C07K 14/395 435/7.21 |
| 7,235,648 B1 | 6/2007 | Fowlkes et al. |
| 7,250,263 B2 | 7/2007 | Klein et al. |
| 7,273,747 B2 | 9/2007 | Manfredi et al. |
| 7,319,009 B2 | 1/2008 | Klein et al. |
| 7,361,498 B2 | 4/2008 | Fowlkes et al. |
| 7,416,881 B1 | 8/2008 | Fowlkes et al. |
| 7,425,445 B2 | 9/2008 | Matsunami et al. |
| 7,611,854 B2 | 11/2009 | Fowlkes et al. |
| 7,691,592 B2 | 4/2010 | Matsunami et al. |
| 7,838,288 B2 | 11/2010 | Matsunami et al. |
| 7,879,565 B2 | 2/2011 | Matsunami et al. |
| 8,298,781 B2 | 10/2012 | Matsunami et al. |
| 9,400,766 B2* | 7/2016 | Chee ..................... G06F 17/00 |
| 9,611,308 B2 | 4/2017 | Matsunami et al. |
| 10,209,239 B1* | 2/2019 | Hanson .............. G01N 33/5008 |
| 2002/0132273 A1* | 9/2002 | Stryer .................. G01N 33/566 435/7.21 |
| 2004/0101447 A1 | 5/2004 | Tajima et al. |
| 2004/0235060 A1 | 11/2004 | Dhanasekaran et al. |
| 2006/0009618 A1 | 1/2006 | Devauchelle et al. |
| 2007/0191257 A1 | 8/2007 | Andretta et al. |
| 2008/0299586 A1 | 12/2008 | Han et al. |
| 2009/0104072 A1 | 4/2009 | Ando et al. |
| 2011/0059544 A1* | 3/2011 | Hong .................. G01N 33/5432 436/149 |
| 2011/0177964 A1 | 7/2011 | Broach et al. |
| 2012/0021932 A1 | 1/2012 | Mershin et al. |
| 2012/0077210 A1 | 3/2012 | Trowell et al. |
| 2013/0216492 A1 | 8/2013 | Kato et al. |
| 2014/0324932 A1 | 10/2014 | Chee et al. |

(Continued)

FOREIGN PATENT DOCUMENTS

| | | |
|---|---|---|
| EP | 2 031 063 A2 | 3/2009 |
| EP | 2 957 283 A1 | 12/2015 |
| WO | WO-00/70343 A2 | 11/2000 |
| WO | WO-00/70343 A3 | 11/2000 |
| WO | WO-01/27158 A2 | 4/2001 |

(Continued)

OTHER PUBLICATIONS

Hanson et al, Anesthesiology, Jan. 2005, 102/1:63-68 (Year: 2005).*
Hockstein et al, Annals of Otology, Rhinology and Laryngology, 2005, 114/7:504-508 (Year: 2005).*
Fukutani et al, Biotechnol. Bioeng., 2012, 109:3143-3151, published online: Jul. 4, 2012 (Year: 2012).*

(Continued)

*Primary Examiner* — Nita M. Minnifield
(74) *Attorney, Agent, or Firm* — Cooley LLP

(57) ABSTRACT

The invention relates to biosensors for detecting odorants, especially a biosensor that mimics odorant detection by a mammal, for example, humans, dogs or cats. The field of the invention also related to the standardization of odors for scent, smell and taste using the biosensor of the invention, and the discovery of agonists, antagonists, and mixtures of odorants for creating new odors, masking odors, enhancing odors, and designing odors.

15 Claims, 1 Drawing Sheet
Specification includes a Sequence Listing.

(56) References Cited

U.S. PATENT DOCUMENTS

| | | | |
|---|---|---|---|
| 2016/0091470 | A1 | 3/2016 | Gafsou |
| 2017/0242004 | A1* | 8/2017 | Hanson ............... G01N 21/77 |
| 2019/0056382 | A1* | 2/2019 | Hanson ............. G01N 33/5008 |
| 2019/0194573 | A1* | 6/2019 | Hanson .................... C11B 9/00 |
| 2019/0194574 | A1* | 6/2019 | Hanson .................... C11B 9/00 |
| 2019/0293628 | A1 | 9/2019 | Hanson et al. |
| 2020/0003774 | A1 | 1/2020 | Hanson et al. |

FOREIGN PATENT DOCUMENTS

| | | | | |
|---|---|---|---|---|
| WO | WO-01/27158 | A3 | 4/2001 | |
| WO | WO-02/068473 | A1 | 9/2002 | |
| WO | WO-2005/051984 | A2 | 6/2005 | |
| WO | WO-2005/051984 | A3 | 6/2005 | |
| WO | WO-2007/121512 | A1 | 11/2007 | |
| WO | WO-2014/165818 | A2 | 10/2014 | |
| WO | WO-2014/165818 | A3 | 10/2014 | |
| WO | WO-2015/102541 | A1 | 7/2015 | |
| WO | WO-2016/030378 | A1 | 3/2016 | |
| WO | WO-2017147323 | A1 * | 8/2017 | ............. G01N 21/77 |

OTHER PUBLICATIONS

Fukutani et al, Analytical Biochemistry, 2015, 471:1-8, available online:Oct. 29, 2014 (Year: 2015).*

Fukutani et al, Biotechnology and Bioengineering, 2012, 109:205-212, published online: Sep. 13, 2011 (Year: 2012).*

Gendron et al, Otolarynology—Head and Neck Surgery, Aug. 2007, 137/:269-273 (Year: 2007).*

Minic et al, FEBS Journal, 2005, 272:524-537 (Year: 2005).*

Misawa et al, J. R. Soc. Interface, 2018, 15:20170952, 17 pages (Year: 2018).*

Zhao et al, Science. Jan. 9, 1998, 279 (5348):237-242 (Year: 1998).*

Pajot-Augy et al, Journal of Receptors and Signal Transduction, 2003, 23/2-3:155-171 (Year: 2003).*

Miranda-Lopez et al, Latest developments in the analysis of aroma compounds, In: Advances in Agriculutral and Food Biotechnology, 2006, pp. 175-192. Editors: Ramon Gerardo Guevara-Gonzalez and Irineo Torres-Pacheco. (Year: 2006).*

Hashi et al, Biotechnology Journal, 2012, 13:1700522, 11 pages (Year: 2012).*

Abaffy, T. (2015). "Human olfactory receptors expression and their role in non-olfactory tissues—A mini review," J. Pharmacogen Pharmacoproteomics 6:4, 7 total pages.

Busse, D. et al. (2014). "A synthetic sandalwood odorant induces wound-healing processes in human keratinocytes via the olfactory receptor OR2AT4," J. Invest. Dermatol. 134:2823-2832.

DeWitt, N. et al. (1999). "GPCR Biosensor Chip," Nature Biotechnology 17:1051.

Ferrer, I, et al. (2016). "Olfactory receptors in non-chemosensory organs: the nervous system in health and disease," Front Aging Neurosci vol. 8, article 163, 17 total pages.

Final Office Action dated Oct. 17, 2018, for U.S. Appl. No. 15/935,025, filed Mar. 25, 2018, 14 pages.

Flegel, C. et al. (2013). "Expression profile of ectopic olfactory receptors determined by deep sequencing," PLoS ONE 8:e55368, 19 total pages.

Gelis L, et al. (2016). "Functional characterization of the odorant receptor 51E2 in human melanocytes," Journal of Biological Chemistry. 291(34):17772-17786.

Greenwood, You Smell Sick: Scientists are racing to create tests that can identify illness via odors in patients sweat, breath and urine, 2016, Scient Am Mind vol. 27, p. 5.

International Search Report dated May 8, 2017, for PCT application No. PCT/US2017/019179, filed on Feb. 23, 2017, 3 pages.

International Search Report dated Dec. 7, 2018, for PCT application No. PCT/US2018/046636, filed on Aug. 14, 2018, 5 pages.

International Search Report dated May 1, 2019, for PCT application No. PCT/US2018/066430, filed on Dec. 19, 2018, 4 pages.

Jovancevic, N. et al. (2017). "Medium-chain fatty acids modulate myocardial function via a cardiac odorant receptor," Basic Research in Cardiology. 112(13) (20 pages).

Kamoun, E.A. et al. (2017). "A review on polymeric hydrogel membranes for wound dressing applications: PVA-based hydrogel dressings," J. Adv Res 8:217-233.

Mainland et al, Human olfactory receptor responses to odorants, 2015, Scientific Data vol. 2, p. 150002.

Martins, S.A.M. et al. (2012). "Towards the miniaturization of GPCR-based live-cell screening assays," Trends in Biotechnology 30:566-574.

Munakata Y, et al. (2018). "Olfactory receptors are expressed in pancreatic β-cells and promote glucose-stimulated insulin secretion," Scientific Reports. 8(1499): 1-11.

Non-Final Office Action dated Jun. 11, 2018, for U.S. Appl. No. 15/927,083, filed Mar. 21, 2018, 10 pages.

Non-Final Office Action dated May 21, 2018, for U.S. Appl. No. 15/935,025, filed Mar. 25, 2018, 11 pages.

Notice of Allowance dated Dec. 13, 2018, for U.S. Appl. No. 15/927,083, filed Mar. 21, 2016, 10 pages.

Pavan, B. et al. (2017). "Potential therapeutic effects of odorants through their ectopic receptors in pigmented cells," Drug Disc Today 22:1123-1130.

Saito, H. et al. (2004). "RTP Family Members induce Functional Expression of Mammalian Odorant Receptors," Cell 119:679-691.

Sasuga, S. et al. (2012). "The Reporter System for GPCR Assay with the Fission Yeast Schizosaccharornyces porribe," Scientifica, pp. 1-11.

Snider et al, Detecting interactions with membrane proteins using a membrane two-hybrid assay in yeast, 2010, Nat Protocol vol. 5, pp. 1281-1293.

Suter et al, Development and application of a DNA microarray-based yeast two-hybrid system, 2013, Nucl Acids Res vol, 41, pp. 1496-1507.

Written Opinion of the International Searching Authority dated May 8, 2017, for PCT application No. PCT/US2017/019179, filed on Feb. 23, 2017, 6 pages.

Written Opinion of the International Searching Authority dated Dec. 7, 2018, for PCT application No. PCT/US2018/046636, filed on Aug. 14, 2018, 6 pages.

Written Opinion of the International Searching Authority dated May 1, 2019, for PCT application No. PCT/US2018/068430, filed on Dec. 19, 2018, 5 pages.

Wu, L. et al. (2012). "Receptor-transporting protein 1 short (RTP1S) mediates translocation and activation of odorant receptors by acting through multiple steps," J. Biol. Chem. 287:22287-22294.

Yamanaka M, et al. (Oct. 27-31, 2013). 17th International Conference on Miniaturized Systems for Chemistry and Life Sciences, pp. 398-400.

Zhuang, H. et al. (2007). "Synergism of accessory factors in functional expression of mammalian odorant receptors," J. Biol. Chem. 282:15284-15293.

Foussat, A. (2015). "La digitalisation des odeurs et du gout transforme la R&D de l'agroalimentaire," The digitalization of smells and tastes is transforming agri-food R&D, with English translation, located at https://web.archive.org/web/20151225203244/http://www.atelier. net:80/trends/articles/digitalisation-odeurs-gout-transforme-rd-de-agroalimentaire_439265#main, 4 total pages.

Glatz, R. et al. (2011). "Mimicking nature's noses: From receptor deorphaning to olfactory biosensing," Progress in Neurobiology 93:270-296.

Hallem, E.A. et al. (2006). "Insect odor and taste receptors," Annu. Rev. Entomol. 51:113-135.

Ko, H.J. et al. (2010). "Specificity of odorant-binding proteins: A factor influencing the sensitivity of olfactory receptor-based biosensors," Bioprocess Biosyst. Eng. 33:55-62.

Non-Final Office Action dated Nov. 13, 2020, for U.S. Appl. No. 16/572,351, filed Sep. 16, 2019, 9 pages.

Non-Final Office Action dated Jan. 30, 2020, for U.S. Appl. No. 16/240,045, filed Jan. 4, 2019, 5 pages.

* cited by examiner

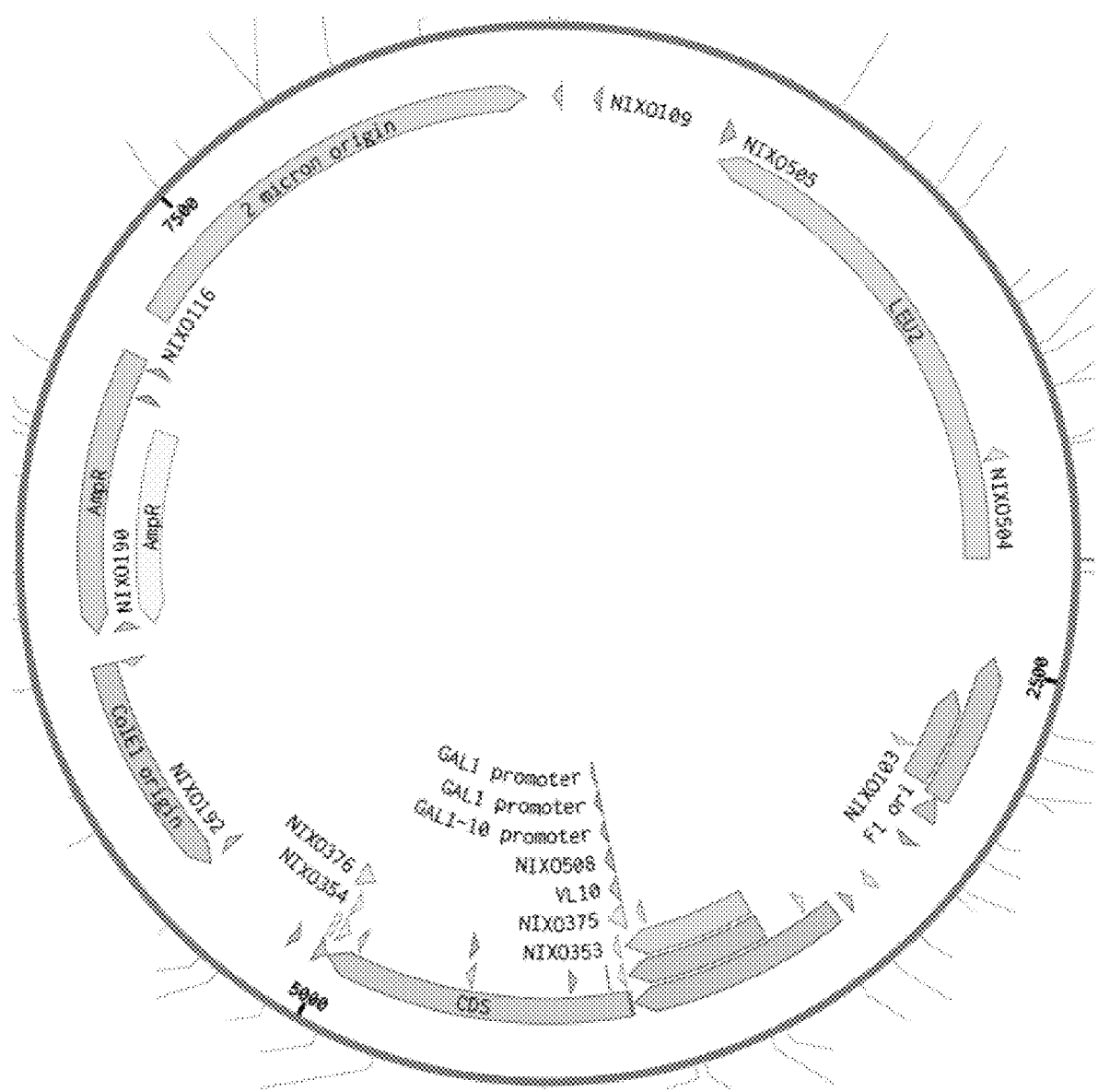

SEQUENCE LISTING

<160> NUMBER OF SEQ ID NOS: 17

<210> SEQ ID NO 1
<211> LENGTH: 8
<212> TYPE: PRT
<213> ORGANISM: Artificial Sequence

```
<220> FEATURE:
<223> OTHER INFORMATION: FLAGTAG

<400> SEQUENCE: 1

Asp Tyr Lys Asp Asp Asp Asp Lys
1               5

<210> SEQ ID NO 2
<211> LENGTH: 10
<212> TYPE: PRT
<213> ORGANISM: Artificial Sequence
<220> FEATURE:
<223> OTHER INFORMATION: OR Motiff

<400> SEQUENCE: 2

Met Ala Tyr Asp Arg Tyr Val Ala Ile Cys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: OR Motiff first Intracellular loop

<400> SEQUENCE: 3

Leu His Thr Pro Met Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: OR Motiff at beginning of TM3

<400> SEQUENCE: 4

Phe Ser Thr Cys Ser Ser His
1               5

<210> SEQ ID NO 5
<211> LENGTH: 6
<212> TYPE: PRT
<213> ORGANISM: Artificial Sequence
<220> FEATURE:
<223> OTHER INFORMATION: OR Motiff in TM7

<400> SEQUENCE: 5

Pro Met Leu Asn Pro Phe
1               5

<210> SEQ ID NO 6
<211> LENGTH: 309
<212> TYPE: PRT
<213> ORGANISM: Homo sapiens

<400> SEQUENCE: 6

Met Arg Glu Asn Asn Gln Ser Ser Thr Leu Glu Phe Ile Leu Leu Gly
1               5                   10                  15

Val Thr Gly Gln Gln Glu Gln Glu Asp Phe Phe Tyr Ile Leu Phe Leu
            20                  25                  30

Phe Ile Tyr Pro Ile Thr Leu Ile Gly Asn Leu Leu Ile Val Leu Ala
        35                  40                  45

Ile Cys Ser Asp Val Arg Leu His Asn Pro Met Tyr Phe Leu Leu Ala
    50                  55                  60
```

```
Asn Leu Ser Leu Val Asp Ile Phe Phe Ser Ser Val Thr Ile Pro Lys
 65                  70                  75                  80

Met Leu Ala Asn His Leu Leu Gly Ser Lys Ser Ile Ser Phe Gly Gly
                 85                  90                  95

Cys Leu Thr Gln Met Tyr Phe Met Ile Ala Leu Gly Asn Thr Asp Ser
            100                 105                 110

Tyr Ile Leu Ala Ala Met Ala Tyr Asp Arg Ala Val Ala Ile Ser Arg
        115                 120                 125

Pro Leu His Tyr Thr Thr Ile Met Ser Pro Arg Ser Cys Ile Trp Leu
130                 135                 140

Ile Ala Gly Ser Trp Val Ile Gly Asn Ala Asn Ala Leu Pro His Thr
145                 150                 155                 160

Leu Leu Thr Ala Ser Leu Ser Phe Cys Gly Asn Gln Glu Val Ala Asn
                165                 170                 175

Phe Tyr Cys Asp Ile Thr Pro Leu Leu Lys Leu Ser Cys Ser Asp Ile
            180                 185                 190

His Phe His Val Lys Met Met Tyr Leu Gly Val Gly Ile Phe Ser Val
        195                 200                 205

Pro Leu Leu Cys Ile Ile Val Ser Tyr Ile Arg Val Phe Ser Thr Val
210                 215                 220

Phe Gln Val Pro Ser Thr Lys Gly Val Leu Lys Ala Phe Ser Thr Cys
225                 230                 235                 240

Gly Ser His Leu Thr Val Val Ser Leu Tyr Tyr Gly Thr Val Met Gly
                245                 250                 255

Thr Tyr Phe Arg Pro Leu Thr Asn Tyr Ser Leu Lys Asp Ala Val Ile
            260                 265                 270

Thr Val Met Tyr Thr Ala Val Thr Pro Met Leu Asn Pro Phe Ile Tyr
        275                 280                 285

Ser Leu Arg Asn Arg Asp Met Lys Ala Ala Leu Arg Lys Leu Phe Asn
290                 295                 300

Lys Arg Ile Ser Ser
305

<210> SEQ ID NO 7
<211> LENGTH: 327
<212> TYPE: PRT
<213> ORGANISM: Homo sapiens

<400> SEQUENCE: 7

Met Glu Trp Arg Asn His Ser Gly Arg Val Ser Glu Phe Val Leu Leu
  1               5                  10                  15

Gly Phe Pro Ala Pro Ala Pro Leu Gln Val Leu Leu Phe Ala Leu Leu
                 20                  25                  30

Leu Leu Ala Tyr Val Leu Val Leu Thr Glu Asn Thr Leu Ile Ile Met
            35                  40                  45

Ala Ile Arg Asn His Ser Thr Leu His Lys Pro Met Tyr Phe Phe Leu
        50                  55                  60

Ala Asn Met Ser Phe Leu Glu Ile Trp Tyr Val Thr Val Thr Ile Pro
 65                  70                  75                  80

Lys Met Leu Ala Gly Phe Val Gly Ser Lys Gln Asp His Gly Gln Leu
                 85                  90                  95

Ile Ser Phe Glu Gly Cys Met Thr Gln Leu Tyr Phe Phe Leu Gly Leu
            100                 105                 110

Gly Cys Thr Glu Cys Val Leu Leu Ala Val Met Ala Tyr Asp Arg Tyr
        115                 120                 125
```

```
Met Ala Ile Cys Tyr Pro Leu His Tyr Pro Val Ile Val Ser Gly Arg
    130                 135                 140

Leu Cys Val Gln Met Ala Ala Gly Ser Trp Ala Gly Gly Phe Gly Ile
145                 150                 155                 160

Ser Met Val Lys Val Phe Leu Ile Ser Gly Leu Ser Tyr Cys Gly Pro
                165                 170                 175

Asn Ile Ile Asn His Phe Phe Cys Asp Val Ser Pro Leu Leu Asn Leu
            180                 185                 190

Ser Cys Thr Asp Met Ser Thr Ala Glu Leu Thr Asp Phe Ile Leu Ala
        195                 200                 205

Ile Phe Ile Leu Leu Gly Pro Leu Ser Val Thr Gly Ala Ser Tyr Val
210                 215                 220

Ala Ile Thr Gly Ala Val Met His Ile Pro Ser Ala Ala Gly Arg Tyr
225                 230                 235                 240

Lys Ala Phe Ser Thr Cys Ala Ser His Leu Thr Val Val Ile Ile Phe
                245                 250                 255

Tyr Ala Ala Ser Ile Phe Ile Tyr Ala Arg Pro Lys Ala Leu Ser Ala
            260                 265                 270

Phe Asp Thr Asn Lys Leu Val Ser Val Leu Tyr Ala Val Ile Val Pro
        275                 280                 285

Leu Leu Asn Pro Ile Ile Tyr Cys Leu Arg Asn Gln Glu Val Lys Arg
290                 295                 300

Ala Leu Cys Cys Thr Leu His Leu Tyr Gln His Gln Asp Pro Asp Pro
305                 310                 315                 320

Lys Lys Ala Ser Arg Asn Val
                325

<210> SEQ ID NO 8
<211> LENGTH: 312
<212> TYPE: PRT
<213> ORGANISM: Homo sapiens

<400> SEQUENCE: 8

Met Met Ile Lys Lys Asn Ala Ser Ser Glu Asp Phe Phe Ile Leu Leu
1               5                   10                  15

Gly Phe Ser Asn Trp Pro Gln Leu Glu Val Val Leu Phe Val Val Ile
                20                  25                  30

Leu Ile Phe Tyr Leu Met Thr Leu Thr Gly Asn Leu Phe Ile Ile Ile
            35                  40                  45

Leu Ser Tyr Val Asp Ser His Leu His Thr Pro Met Tyr Phe Phe Leu
        50                  55                  60

Ser Asn Leu Ser Phe Leu Asp Leu Cys Tyr Thr Thr Ser Ser Ile Pro
65                  70                  75                  80

Gln Leu Leu Val Asn Leu Arg Gly Pro Glu Lys Thr Ile Ser Tyr Ala
                85                  90                  95

Gly Cys Met Val Gln Leu Tyr Phe Val Leu Ala Leu Gly Ile Thr Glu
            100                 105                 110

Cys Val Leu Leu Val Val Met Ser Tyr Asp Arg Tyr Val Ala Val Cys
        115                 120                 125

Arg Pro Leu His Tyr Thr Val Leu Met His Pro Arg Phe Cys His Leu
    130                 135                 140

Leu Val Ala Ala Ser Trp Val Ile Gly Phe Thr Ile Ser Ala Leu His
145                 150                 155                 160

Ser Ser Phe Thr Phe Trp Val Pro Leu Cys Gly His Arg Leu Val Asp
                165                 170                 175
```

His Phe Phe Cys Glu Val Pro Ala Leu Leu Arg Leu Ser Cys Val Asp
                180                 185                 190

Thr His Ala Asn Glu Leu Thr Leu Met Val Met Ser Ser Ile Phe Val
            195                 200                 205

Leu Ile Pro Leu Ile Leu Ile Leu Thr Thr Tyr Gly Ala Ile Ala Arg
        210                 215                 220

Ala Val Leu Ser Met Gln Ser Thr Thr Gly Leu Gln Lys Val Phe Arg
225                 230                 235                 240

Thr Cys Gly Ala His Leu Met Val Val Ser Leu Phe Phe Ile Pro Val
                245                 250                 255

Met Cys Met Tyr Leu Gln Pro Pro Ser Glu Asn Ser Pro Asp Gln Gly
            260                 265                 270

Lys Phe Ile Ala Leu Phe Tyr Thr Val Val Thr Pro Ser Leu Asn Pro
        275                 280                 285

Leu Ile Tyr Thr Leu Arg Asn Lys His Val Lys Gly Ala Ala Lys Arg
    290                 295                 300

Leu Leu Gly Trp Glu Trp Gly Lys
305                 310

<210> SEQ ID NO 9
<211> LENGTH: 320
<212> TYPE: PRT
<213> ORGANISM: Homo sapiens

<400> SEQUENCE: 9

Met Asp Gln Ser Asn Tyr Ser Ser Leu His Gly Phe Ile Leu Leu Gly
1               5                   10                  15

Phe Ser Asn His Pro Lys Met Glu Met Ile Leu Ser Gly Val Val Ala
            20                  25                  30

Ile Phe Tyr Leu Ile Thr Leu Val Gly Asn Thr Ala Ile Ile Leu Ala
        35                  40                  45

Ser Leu Leu Asp Ser Gln Leu His Thr Pro Met Tyr Phe Phe Leu Arg
    50                  55                  60

Asn Leu Ser Phe Leu Asp Leu Cys Phe Thr Thr Ser Ile Ile Pro Gln
65                  70                  75                  80

Met Leu Val Asn Leu Trp Gly Pro Asp Lys Thr Ile Ser Tyr Val Gly
                85                  90                  95

Cys Ile Ile Gln Leu Tyr Val Tyr Met Trp Leu Gly Ser Val Glu Cys
            100                 105                 110

Leu Leu Leu Ala Val Met Ser Tyr Asp Arg Phe Thr Ala Ile Cys Lys
        115                 120                 125

Pro Leu His Tyr Phe Val Val Met Asn Pro His Leu Cys Leu Lys Met
    130                 135                 140

Ile Ile Met Ile Trp Ser Ile Ser Leu Ala Asn Ser Val Val Leu Cys
145                 150                 155                 160

Thr Leu Thr Leu Asn Leu Pro Thr Cys Gly Asn Asn Ile Leu Asp His
                165                 170                 175

Phe Leu Cys Glu Leu Pro Ala Leu Val Lys Ile Ala Cys Val Asp Thr
            180                 185                 190

Thr Thr Val Glu Met Ser Val Phe Ala Leu Gly Ile Ile Ile Val Leu
        195                 200                 205

Thr Pro Leu Ile Leu Ile Leu Ile Ser Tyr Gly Tyr Ile Ala Lys Ala
    210                 215                 220

Val Leu Arg Thr Lys Ser Lys Ala Ser Gln Arg Lys Ala Met Asn Thr
225                 230                 235                 240

```
Cys Gly Ser His Leu Thr Val Val Ser Met Phe Gly Thr Ile Ile
                245                 250                 255

Tyr Met Tyr Leu Gln Pro Gly Asn Arg Ala Ser Lys Asp Gln Gly Lys
            260                 265                 270

Phe Leu Thr Leu Phe Tyr Thr Val Ile Thr Pro Ser Leu Asn Pro Leu
            275                 280                 285

Ile Tyr Thr Leu Arg Asn Lys Asp Met Lys Asp Ala Leu Lys Lys Leu
            290                 295                 300

Met Arg Phe His His Lys Ser Thr Lys Ile Lys Arg Asn Cys Lys Ser
305                 310                 315                 320

<210> SEQ ID NO 10
<211> LENGTH: 311
<212> TYPE: PRT
<213> ORGANISM: Homo sapiens

<400> SEQUENCE: 10

Met Gly Thr Gly Asn Asp Thr Val Val Glu Phe Thr Leu Leu Gly
1                   5                   10                  15

Leu Ser Glu Asp Thr Thr Val Cys Ala Ile Leu Phe Leu Val Phe Leu
                20                  25                  30

Gly Ile Tyr Val Val Thr Leu Met Gly Asn Ile Ser Ile Val Leu
            35                  40                  45

Ile Arg Arg Ser His His Leu His Thr Pro Met Tyr Ile Phe Leu Cys
    50                  55                  60

His Leu Ala Phe Val Asp Ile Gly Tyr Ser Ser Ser Val Thr Pro Val
65                  70                  75                  80

Met Leu Met Ser Phe Leu Arg Lys Glu Thr Ser Leu Pro Val Ala Gly
                85                  90                  95

Cys Val Ala Gln Leu Cys Ser Val Val Thr Phe Gly Thr Ala Glu Cys
            100                 105                 110

Phe Leu Leu Ala Ala Met Ala Tyr Asp Arg Tyr Val Ala Ile Cys Ser
            115                 120                 125

Pro Leu Leu Tyr Ser Thr Cys Met Ser Pro Gly Val Cys Ile Ile Leu
            130                 135                 140

Val Gly Met Ser Tyr Leu Gly Gly Cys Val Asn Ala Trp Thr Phe Ile
145                 150                 155                 160

Gly Cys Leu Leu Arg Leu Ser Phe Cys Gly Pro Asn Lys Val Asn His
                165                 170                 175

Phe Phe Cys Asp Tyr Ser Pro Leu Leu Lys Leu Ala Cys Ser His Asp
            180                 185                 190

Phe Thr Phe Glu Ile Ile Pro Ala Ile Ser Ser Gly Ser Ile Ile Val
            195                 200                 205

Ala Thr Val Cys Val Ile Ala Ile Ser Tyr Ile Tyr Ile Leu Ile Thr
            210                 215                 220

Ile Leu Lys Met His Ser Thr Lys Gly Arg His Lys Ala Phe Ser Thr
225                 230                 235                 240

Cys Thr Ser His Leu Thr Ala Val Thr Leu Phe Tyr Gly Thr Ile Thr
                245                 250                 255

Phe Ile Tyr Val Met Pro Lys Ser Ser Tyr Ser Thr Asp Gln Asn Lys
            260                 265                 270

Val Val Ser Val Phe Tyr Thr Val Ile Pro Met Leu Asn Pro Leu
            275                 280                 285
```

Ile Tyr Ser Leu Arg Asn Lys Glu Ile Lys Gly Ala Leu Lys Arg Glu
            290                 295                 300

Leu Arg Ile Lys Ile Phe Ser
305                 310

<210> SEQ ID NO 11
<211> LENGTH: 100
<212> TYPE: PRT
<213> ORGANISM: Artificial Sequence
<220> FEATURE:
<223> OTHER INFORMATION: N terminal sequence of rat RI7

<400> SEQUENCE: 11

Met Glu Arg Arg Asn His Ser Gly Arg Val Ser Glu Phe Val Leu Leu
1               5                   10                  15

Gly Phe Pro Ala Pro Ala Pro Leu Arg Val Leu Leu Phe Phe Leu Ser
            20                  25                  30

Leu Leu Ala Tyr Val Leu Val Leu Thr Glu Asn Met Leu Ile Ile Ile
            35                  40                  45

Ala Ile Arg Asn His Pro Thr Leu His Lys Pro Met Tyr Phe Phe Leu
        50                  55                  60

Ala Asn Met Ser Phe Leu Glu Ile Trp Tyr Val Thr Val Thr Ile Pro
65                  70                  75                  80

Lys Met Leu Ala Gly Phe Ile Gly Ser Lys Glu Asn His Gly Gln Leu
                85                  90                  95

Ile Ser Phe Glu
            100

<210> SEQ ID NO 12
<211> LENGTH: 309
<212> TYPE: PRT
<213> ORGANISM: Artificial Sequence
<220> FEATURE:
<223> OTHER INFORMATION: Fusion of human OR6A2 and OR1A1

<400> SEQUENCE: 12

Met Glu Trp Arg Asn His Ser Gly Arg Val Ser Glu Phe Val Leu Leu
1               5                   10                  15

Gly Phe Pro Ala Pro Ala Pro Leu Gln Val Leu Leu Phe Ala Leu Leu
            20                  25                  30

Leu Leu Ala Tyr Val Leu Val Leu Thr Glu Asn Thr Leu Ile Ile Met
            35                  40                  45

Ala Ile Arg Asn His Ser Thr His Asn Pro Met Tyr Phe Leu Leu Ala
        50                  55                  60

Asn Leu Ser Leu Val Asp Ile Phe Phe Ser Ser Val Thr Ile Pro Lys
65                  70                  75                  80

Met Leu Ala Asn His Leu Leu Gly Ser Lys Ser Ile Ser Phe Gly Gly
                85                  90                  95

Cys Leu Thr Gln Met Tyr Phe Met Ile Ala Leu Gly Asn Thr Asp Ser
                100                 105                 110

Tyr Ile Leu Ala Ala Met Ala Tyr Asp Arg Ala Val Ala Ile Ser Arg
            115                 120                 125

Pro Leu His Tyr Thr Thr Ile Met Ser Pro Arg Ser Cys Ile Trp Leu
        130                 135                 140

Ile Ala Gly Ser Trp Val Ile Gly Asn Ala Asn Ala Leu Pro His Thr
145                 150                 155                 160

Leu Leu Thr Ala Ser Leu Ser Phe Cys Gly Asn Gln Glu Val Ala Asn
                165                 170                 175

```
Phe Tyr Cys Asp Ile Thr Pro Leu Leu Lys Leu Ser Cys Ser Asp Ile
            180                 185                 190

His Phe His Val Lys Met Met Tyr Leu Gly Val Gly Ile Phe Ser Val
        195                 200                 205

Pro Leu Leu Cys Ile Ile Val Ser Tyr Ile Arg Val Phe Ser Thr Val
    210                 215                 220

Phe Gln Val Pro Ser Thr Lys Gly Val Leu Lys Ala Phe Ser Thr Cys
225                 230                 235                 240

Gly Ser His Leu Thr Val Val Ser Leu Tyr Tyr Gly Thr Val Met Gly
                245                 250                 255

Thr Tyr Phe Arg Pro Leu Thr Asn Tyr Ser Leu Lys Asp Ala Val Ile
            260                 265                 270

Thr Val Met Tyr Thr Ala Val Thr Pro Met Leu Asn Pro Phe Ile Tyr
        275                 280                 285

Ser Leu Arg Asn Arg Asp Met Lys Ala Ala Leu Arg Lys Leu Phe Asn
    290                 295                 300

Lys Arg Ile Ser Ser
305

<210> SEQ ID NO 13
<211> LENGTH: 381
<212> TYPE: PRT
<213> ORGANISM: Homo sapiens

<400> SEQUENCE: 13

Met Gly Cys Leu Gly Gly Asn Ser Lys Thr Thr Glu Asp Gln Gly Val
1               5                   10                  15

Asp Glu Lys Glu Arg Arg Glu Ala Asn Lys Lys Ile Glu Lys Gln Leu
            20                  25                  30

Gln Lys Glu Arg Leu Ala Tyr Lys Ala Thr His Arg Leu Leu Leu Leu
        35                  40                  45

Gly Ala Gly Glu Ser Gly Lys Ser Thr Ile Val Lys Gln Met Arg Ile
    50                  55                  60

Leu His Val Asn Gly Phe Asn Pro Glu Glu Lys Lys Gln Lys Ile Leu
65                  70                  75                  80

Asp Ile Arg Lys Asn Val Lys Asp Ala Ile Val Thr Ile Val Ser Ala
                85                  90                  95

Met Ser Thr Ile Ile Pro Pro Val Pro Leu Ala Asn Pro Glu Asn Gln
            100                 105                 110

Phe Arg Ser Asp Tyr Ile Lys Ser Ile Ala Pro Ile Thr Asp Phe Glu
        115                 120                 125

Tyr Ser Gln Glu Phe Phe Asp His Val Lys Lys Leu Trp Asp Asp Glu
    130                 135                 140

Gly Val Lys Ala Cys Phe Glu Arg Ser Asn Glu Tyr Gln Leu Ile Asp
145                 150                 155                 160

Cys Ala Gln Tyr Phe Leu Glu Arg Ile Asp Ser Val Ser Leu Val Asp
                165                 170                 175

Tyr Thr Pro Thr Asp Gln Asp Leu Leu Arg Cys Arg Val Leu Thr Ser
            180                 185                 190

Gly Ile Phe Glu Thr Arg Phe Gln Val Asp Lys Val Asn Phe His Met
        195                 200                 205

Phe Asp Val Gly Gly Gln Arg Asp Glu Arg Arg Lys Trp Ile Gln Cys
    210                 215                 220

Phe Asn Asp Val Thr Ala Ile Ile Tyr Val Ala Ala Cys Ser Ser Tyr
225                 230                 235                 240
```

```
Asn Met Val Ile Arg Glu Asp Asn Asn Thr Asn Arg Leu Arg Glu Ser
            245                 250                 255

Leu Asp Leu Phe Glu Ser Ile Trp Asn Asn Arg Trp Leu Arg Thr Ile
        260                 265                 270

Ser Ile Ile Leu Phe Leu Asn Lys Gln Asp Met Leu Ala Glu Lys Val
    275                 280                 285

Leu Ala Gly Lys Ser Lys Ile Glu Asp Tyr Phe Pro Glu Tyr Ala Asn
290                 295                 300

Tyr Thr Val Pro Glu Asp Ala Thr Pro Asp Ala Gly Glu Asp Pro Lys
305                 310                 315                 320

Val Thr Arg Ala Lys Phe Phe Ile Arg Asp Leu Phe Leu Arg Ile Ser
                325                 330                 335

Thr Ala Thr Gly Asp Gly Lys His Tyr Cys Tyr Pro His Phe Thr Cys
            340                 345                 350

Ala Val Asp Thr Glu Asn Ile Arg Arg Val Phe Asn Asp Cys Arg Asp
        355                 360                 365

Ile Ile Gln Arg Met His Leu Lys Gln Tyr Glu Leu Leu
    370                 375                 380

<210> SEQ ID NO 14
<211> LENGTH: 340
<212> TYPE: PRT
<213> ORGANISM: Homo sapiens

<400> SEQUENCE: 14

Met Ser Glu Leu Glu Gln Leu Arg Gln Glu Ala Glu Gln Leu Arg Asn
1               5                   10                  15

Gln Ile Arg Asp Ala Arg Lys Ala Cys Gly Asp Ser Thr Leu Thr Gln
            20                  25                  30

Ile Thr Ala Gly Leu Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val
            100                 105                 110

Ala Cys Gly Gly Leu Asp Asn Ile Cys Ser Ile Tyr Ser Leu Lys Thr
        115                 120                 125

Arg Glu Gly Asn Val Arg Val Ser Arg Glu Leu Pro Gly His Thr Gly
    130                 135                 140

Tyr Leu Ser Cys Cys Arg Phe Leu Asp Asp Asn Gln Ile Ile Thr Ser
145                 150                 155                 160

Ser Gly Asp Thr Thr Cys Ala Leu Trp Asp Ile Glu Thr Gly Gln Gln
                165                 170                 175

Thr Val Gly Phe Ala Gly His Ser Gly Asp Val Met Ser Leu Ser Leu
            180                 185                 190

Ala Pro Asp Gly Arg Thr Phe Val Ser Gly Ala Cys Asp Ala Ser Ile
        195                 200                 205

Lys Leu Trp Asp Val Arg Asp Ser Met Cys Arg Gln Thr Phe Ile Gly
    210                 215                 220

His Glu Ser Asp Ile Asn Ala Val Ala Phe Phe Pro Asn Gly Tyr Ala
225                 230                 235                 240
```

```
Phe Thr Thr Gly Ser Asp Asp Ala Thr Cys Arg Leu Phe Asp Leu Arg
                245                 250                 255

Ala Asp Gln Glu Leu Leu Met Tyr Ser His Asp Asn Ile Ile Cys Gly
            260                 265                 270

Ile Thr Ser Val Ala Phe Ser Arg Ser Gly Arg Leu Leu Leu Ala Gly
        275                 280                 285

Tyr Asp Asp Phe Asn Cys Asn Ile Trp Asp Ala Met Lys Gly Asp Arg
    290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 15
<211> LENGTH: 68
<212> TYPE: PRT
<213> ORGANISM: Homo sapiens

<400> SEQUENCE: 15

Met Ser Gly Ser Ser Val Ala Ala Met Lys Lys Val Val Gln Gln
1               5                   10                  15

Leu Arg Leu Glu Ala Gly Leu Asn Arg Val Lys Val Ser Gln Ala Ala
            20                  25                  30

Ala Asp Leu Lys Gln Phe Cys Leu Gln Asn Ala Gln His Asp Pro Leu
        35                  40                  45

Leu Thr Gly Val Ser Ser Thr Asn Pro Phe Arg Pro Gln Lys Val
    50                  55                  60

Cys Ser Phe Leu
65

<210> SEQ ID NO 16
<211> LENGTH: 1144
<212> TYPE: PRT
<213> ORGANISM: Homo sapiens

<400> SEQUENCE: 16

Met Pro Arg Asn Gln Gly Phe Ser Glu Pro Glu Tyr Ser Ala Glu Tyr
1               5                   10                  15

Ser Ala Glu Tyr Ser Val Ser Leu Pro Ser Asp Pro Arg Gly Val
            20                  25                  30

Gly Arg Thr His Glu Ile Ser Val Arg Asn Ser Gly Ser Cys Leu Cys
        35                  40                  45

Leu Pro Arg Phe Met Arg Leu Thr Phe Val Pro Glu Ser Leu Glu Asn
    50                  55                  60

Leu Tyr Gln Thr Tyr Phe Lys Arg Gln Arg His Glu Thr Leu Leu Val
65                  70                  75                  80

Leu Val Val Phe Ala Ala Leu Phe Asp Cys Tyr Val Val Met Cys
            85                  90                  95

Ala Val Val Phe Ser Ser Asp Lys Leu Ala Ser Leu Ala Val Ala Gly
            100                 105                 110

Ile Gly Leu Val Leu Asp Ile Ile Leu Phe Val Leu Cys Lys Lys Gly
        115                 120                 125

Leu Leu Pro Asp Arg Val Thr Arg Arg Val Leu Pro Tyr Val Leu Trp
    130                 135                 140
```

```
Leu Leu Ile Thr Ala Gln Ile Phe Ser Tyr Leu Gly Leu Asn Phe Ala
145                 150                 155                 160

Arg Ala His Ala Ala Ser Asp Thr Val Gly Trp Gln Val Phe Phe Val
            165                 170                 175

Phe Ser Phe Phe Ile Thr Leu Pro Leu Ser Leu Ser Pro Ile Val Ile
                180                 185                 190

Ile Ser Val Val Ser Cys Val His Thr Leu Val Leu Gly Val Thr
                195                 200                 205

Val Ala Gln Gln Gln Gln Glu Leu Lys Gly Met Gln Leu Leu Arg
210                 215                 220

Glu Ile Leu Ala Asn Val Phe Leu Tyr Leu Cys Ala Ile Ala Val Gly
225                 230                 235                 240

Ile Met Ser Tyr Tyr Met Ala Asp Arg Lys His Arg Lys Ala Phe Leu
                245                 250                 255

Glu Ala Arg Gln Ser Leu Glu Val Lys Met Asn Leu Glu Glu Gln Ser
                260                 265                 270

Gln Gln Gln Glu Asn Leu Met Leu Ser Ile Leu Pro Lys His Val Ala
            275                 280                 285

Asp Glu Met Leu Lys Asp Met Lys Lys Asp Glu Ser Gln Lys Asp Gln
290                 295                 300

Gln Gln Phe Asn Thr Met Tyr Met Tyr Arg His Glu Asn Val Ser Ile
305                 310                 315                 320

Leu Phe Ala Asp Ile Val Gly Phe Thr Gln Leu Ser Ser Ala Cys Ser
                325                 330                 335

Ala Gln Glu Leu Val Lys Leu Leu Asn Glu Leu Phe Ala Arg Phe Asp
            340                 345                 350

Lys Leu Ala Ala Lys Tyr His Gln Leu Arg Ile Lys Ile Leu Gly Asp
            355                 360                 365

Cys Tyr Tyr Cys Ile Cys Gly Leu Pro Asp Tyr Arg Glu Asp His Ala
            370                 375                 380

Val Cys Ser Ile Leu Met Gly Leu Ala Met Val Glu Ala Ile Ser Tyr
385                 390                 395                 400

Val Arg Glu Lys Thr Lys Thr Gly Val Asp Met Arg Val Gly Val His
                405                 410                 415

Thr Gly Thr Val Leu Gly Gly Val Leu Gly Gln Lys Arg Trp Gln Tyr
                420                 425                 430

Asp Val Trp Ser Thr Asp Val Thr Val Ala Asn Lys Met Glu Ala Gly
            435                 440                 445

Gly Ile Pro Gly Arg Val His Ile Ser Gln Ser Thr Met Asp Cys Leu
450                 455                 460

Lys Gly Glu Phe Asp Val Glu Pro Gly Asp Gly Gly Ser Arg Cys Asp
465                 470                 475                 480

Tyr Leu Glu Glu Lys Gly Ile Glu Thr Tyr Leu Ile Ile Ala Ser Lys
                485                 490                 495

Pro Glu Val Lys Lys Thr Ala Thr Gln Asn Gly Leu Asn Gly Ser Ala
            500                 505                 510

Leu Pro Asn Gly Ala Pro Ala Ser Ser Lys Ser Ser Pro Ala Leu
            515                 520                 525

Ile Glu Thr Lys Glu Pro Asn Gly Ser Ala His Ser Ser Gly Ser Thr
        530                 535                 540

Ser Glu Lys Pro Glu Glu Gln Asp Ala Gln Ala Asp Asn Pro Ser Phe
545                 550                 555                 560
```

-continued

Pro Asn Pro Arg Arg Arg Leu Arg Leu Gln Asp Leu Ala Asp Arg Val
                565                 570                 575

Val Asp Ala Ser Glu Asp Glu His Glu Leu Asn Gln Leu Leu Asn Glu
            580                 585                 590

Ala Leu Leu Glu Arg Glu Ser Ala Gln Val Val Lys Lys Arg Asn Thr
        595                 600                 605

Phe Leu Leu Ser Met Arg Phe Met Asp Pro Glu Met Glu Thr Arg Tyr
    610                 615                 620

Ser Val Glu Lys Glu Lys Gln Ser Gly Ala Ala Phe Ser Cys Ser Cys
625                 630                 635                 640

Val Val Leu Leu Cys Thr Ala Leu Val Glu Ile Leu Ile Asp Pro Trp
            645                 650                 655

Leu Met Thr Asn Tyr Val Thr Phe Met Val Gly Glu Ile Leu Leu Leu
        660                 665                 670

Ile Leu Thr Ile Cys Ser Leu Ala Ala Ile Phe Pro Arg Ala Phe Pro
    675                 680                 685

Lys Lys Leu Val Ala Phe Ser Thr Trp Ile Asp Arg Thr Arg Trp Ala
690                 695                 700

Arg Asn Thr Trp Ala Met Leu Ala Ile Phe Ile Leu Val Met Ala Asn
705                 710                 715                 720

Val Val Asp Met Leu Ser Cys Leu Gln Tyr Tyr Thr Gly Pro Ser Asn
            725                 730                 735

Ala Thr Ala Gly Met Glu Thr Glu Gly Ser Cys Leu Glu Asn Pro Lys
        740                 745                 750

Tyr Tyr Asn Tyr Val Ala Val Leu Ser Leu Ile Ala Thr Ile Met Leu
    755                 760                 765

Val Gln Val Ser His Met Val Lys Leu Thr Leu Met Leu Leu Val Ala
    770                 775                 780

Gly Ala Val Ala Thr Ile Asn Leu Tyr Ala Trp Arg Pro Val Phe Asp
785                 790                 795                 800

Glu Tyr Asp His Lys Arg Phe Arg Glu His Asp Leu Pro Met Val Ala
            805                 810                 815

Leu Glu Gln Met Gln Gly Phe Asn Pro Gly Leu Asn Gly Thr Asp Arg
        820                 825                 830

Leu Pro Leu Val Pro Ser Lys Tyr Ser Met Thr Val Met Val Phe Leu
    835                 840                 845

Met Met Leu Ser Phe Tyr Tyr Phe Ser Arg His Val Glu Lys Leu Ala
850                 855                 860

Arg Thr Leu Phe Leu Trp Lys Ile Glu Val His Asp Gln Lys Glu Arg
865                 870                 875                 880

Val Tyr Glu Met Arg Arg Trp Asn Glu Ala Leu Val Thr Asn Met Leu
            885                 890                 895

Pro Glu His Val Ala Arg His Phe Leu Gly Ser Lys Lys Arg Asp Glu
        900                 905                 910

Glu Leu Tyr Ser Gln Thr Tyr Asp Glu Ile Gly Val Met Phe Ala Ser
    915                 920                 925

Leu Pro Asn Phe Ala Asp Phe Tyr Thr Glu Ser Ile Asn Asn Gly
    930                 935                 940

Gly Ile Glu Cys Leu Arg Phe Leu Asn Glu Ile Ile Ser Asp Phe Asp
945                 950                 955                 960

Ser Leu Leu Asp Asn Pro Lys Phe Arg Val Ile Thr Lys Ile Lys Thr
            965                 970                 975

Ile Gly Ser Thr Tyr Met Ala Ala Ser Gly Val Thr Pro Asp Val Asn
            980                 985                 990

Thr Asn Gly Phe Ala Ser Ser Asn Lys Glu Asp Lys Ser Glu Arg Glu
        995                 1000                1005

Arg Trp Gln His Leu Ala Asp Leu Ala Asp Phe Ala Leu Ala Met
    1010                1015                1020

Lys Asp Thr Leu Thr Asn Ile Asn Asn Gln Ser Phe Asn Asn Phe
    1025                1030                1035

Met Leu Arg Ile Gly Met Asn Lys Gly Val Leu Ala Gly Val
    1040                1045                1050

Ile Gly Ala Arg Lys Pro His Tyr Asp Ile Trp Gly Asn Thr Val
    1055                1060                1065

Asn Val Ala Ser Arg Met Glu Ser Thr Gly Val Met Gly Asn Ile
    1070                1075                1080

Gln Val Val Glu Glu Thr Gln Val Ile Leu Arg Glu Tyr Gly Phe
    1085                1090                1095

Arg Phe Val Arg Arg Gly Pro Ile Phe Val Lys Gly Lys Gly Glu
    1100                1105                1110

Leu Leu Thr Phe Phe Leu Lys Gly Arg Asp Lys Leu Ala Thr Phe
    1115                1120                1125

Pro Asn Gly Pro Ser Val Thr Leu Pro His Gln Val Val Asp Asn
    1130                1135                1140

Ser

<210> SEQ ID NO 17
<211> LENGTH: 1144
<212> TYPE: PRT
<213> ORGANISM: Homo sapiens

<400> SEQUENCE: 17

Met Pro Arg Asn Gln Gly Phe Ser Glu Pro Glu Tyr Ser Ala Glu Tyr
1               5                   10                  15

Ser Ala Glu Tyr Ser Val Ser Leu Pro Ser Asp Pro Asp Arg Gly Val
            20                  25                  30

Gly Arg Thr His Glu Ile Ser Val Arg Asn Ser Gly Ser Cys Leu Cys
        35                  40                  45

Leu Pro Arg Phe Met Arg Leu Thr Phe Val Pro Glu Ser Leu Glu Asn
    50                  55                  60

Leu Tyr Gln Thr Tyr Phe Lys Arg Gln Arg His Glu Thr Leu Leu Val
65                  70                  75                  80

Leu Val Val Phe Ala Ala Leu Phe Asp Cys Tyr Val Val Met Cys
            85                  90                  95

Ala Val Val Phe Ser Ser Asp Lys Leu Ala Ser Leu Ala Val Ala Gly
                100                 105                 110

Ile Gly Leu Val Leu Asp Ile Ile Leu Phe Val Leu Cys Lys Lys Gly
            115                 120                 125

Leu Leu Pro Asp Arg Val Thr Arg Arg Val Leu Pro Tyr Val Leu Trp
    130                 135                 140

Leu Leu Ile Thr Ala Gln Ile Phe Ser Tyr Leu Gly Leu Asn Phe Ala
145                 150                 155                 160

Arg Ala His Ala Ala Ser Asp Thr Val Gly Trp Gln Val Phe Phe Val
                165                 170                 175

Phe Ser Phe Phe Ile Thr Leu Pro Leu Ser Leu Ser Pro Ile Val Ile
            180                 185                 190

```
Ile Ser Val Val Ser Cys Val Val His Thr Leu Val Leu Gly Val Thr
            195                 200                 205

Val Ala Gln Gln Gln Gln Glu Glu Leu Lys Gly Met Gln Leu Leu Arg
210                 215                 220

Glu Ile Leu Ala Asn Val Phe Leu Tyr Leu Cys Ala Ile Ala Val Gly
225                 230                 235                 240

Ile Met Ser Tyr Tyr Met Ala Asp Arg Lys His Arg Lys Ala Phe Leu
            245                 250                 255

Glu Ala Arg Gln Ser Leu Glu Val Lys Met Asn Leu Glu Glu Gln Ser
        260                 265                 270

Gln Gln Gln Glu Asn Leu Met Leu Ser Ile Leu Pro Lys His Val Ala
    275                 280                 285

Asp Glu Met Leu Lys Asp Met Lys Lys Asp Glu Ser Gln Lys Asp Gln
290                 295                 300

Gln Gln Phe Asn Thr Met Tyr Met Tyr Arg His Glu Asn Val Ser Ile
305                 310                 315                 320

Leu Phe Ala Asp Ile Val Gly Phe Thr Gln Leu Ser Ser Ala Cys Ser
            325                 330                 335

Ala Gln Glu Leu Val Lys Leu Leu Asn Glu Leu Phe Ala Arg Phe Asp
        340                 345                 350

Lys Leu Ala Ala Lys Tyr His Gln Leu Arg Ile Lys Ile Leu Gly Asp
    355                 360                 365

Cys Tyr Tyr Cys Ile Cys Gly Leu Pro Asp Tyr Arg Glu Asp His Ala
370                 375                 380

Val Cys Ser Ile Leu Met Gly Leu Ala Met Val Glu Ala Ile Ser Tyr
385                 390                 395                 400

Val Arg Glu Lys Thr Lys Thr Gly Val Asp Met Arg Val Gly Val His
            405                 410                 415

Thr Gly Thr Val Leu Gly Gly Val Leu Gly Gln Lys Arg Trp Gln Tyr
        420                 425                 430

Asp Val Trp Ser Thr Asp Val Thr Val Ala Asn Lys Met Glu Ala Gly
    435                 440                 445

Gly Ile Pro Gly Arg Val His Ile Ser Gln Ser Thr Met Asp Cys Leu
450                 455                 460

Lys Gly Glu Phe Asp Val Glu Pro Gly Asp Gly Gly Ser Arg Cys Asp
465                 470                 475                 480

Tyr Leu Glu Glu Lys Gly Ile Glu Thr Tyr Leu Ile Ile Ala Ser Lys
            485                 490                 495

Pro Glu Val Lys Lys Thr Ala Thr Gln Asn Gly Leu Asn Gly Ser Ala
        500                 505                 510

Leu Pro Asn Gly Ala Pro Ala Ser Lys Ser Ser Pro Ala Leu
    515                 520                 525

Ile Glu Thr Lys Glu Pro Asn Gly Ser Ala His Ser Ser Gly Ser Thr
530                 535                 540

Ser Glu Lys Pro Glu Glu Gln Asp Ala Gln Ala Asp Asn Pro Ser Phe
545                 550                 555                 560

Pro Asn Pro Arg Arg Arg Leu Arg Leu Gln Asp Leu Ala Asp Arg Val
            565                 570                 575

Val Asp Ala Ser Glu Asp Glu His Glu Leu Asn Gln Leu Leu Asn Glu
        580                 585                 590

Ala Leu Leu Glu Arg Glu Ser Ala Gln Val Val Lys Lys Arg Asn Thr
    595                 600                 605
```

```
Phe Leu Leu Ser Met Arg Phe Met Asp Pro Glu Met Glu Thr Arg Tyr
610                 615                 620

Ser Val Glu Lys Glu Lys Gln Ser Gly Ala Ala Phe Ser Cys Ser Cys
625                 630                 635                 640

Val Val Leu Leu Cys Thr Ala Leu Val Glu Ile Leu Ile Asp Pro Trp
                645                 650                 655

Leu Met Thr Asn Tyr Val Thr Phe Met Val Gly Glu Ile Leu Leu Leu
                660                 665                 670

Ile Leu Thr Ile Cys Ser Leu Ala Ala Ile Phe Pro Arg Ala Phe Pro
                675                 680                 685

Lys Lys Leu Val Ala Phe Ser Thr Trp Ile Asp Arg Thr Arg Trp Ala
690                 695                 700

Arg Asn Thr Trp Ala Met Leu Ala Ile Phe Ile Leu Val Met Ala Asn
705                 710                 715                 720

Val Val Asp Met Leu Ser Cys Leu Gln Tyr Tyr Thr Gly Pro Ser Asn
                725                 730                 735

Ala Thr Ala Gly Met Glu Thr Glu Gly Ser Cys Leu Glu Asn Pro Lys
                740                 745                 750

Tyr Tyr Asn Tyr Val Ala Val Leu Ser Leu Ile Ala Thr Ile Met Leu
                755                 760                 765

Val Gln Val Ser His Met Val Lys Leu Thr Leu Met Leu Leu Val Ala
770                 775                 780

Gly Ala Val Ala Thr Ile Asn Leu Tyr Ala Trp Arg Pro Val Phe Asp
785                 790                 795                 800

Glu Tyr Asp His Lys Arg Phe Arg Glu His Asp Leu Pro Met Val Ala
                805                 810                 815

Leu Glu Gln Met Gln Gly Phe Asn Pro Gly Leu Asn Gly Thr Asp Arg
                820                 825                 830

Leu Pro Leu Val Pro Ser Lys Tyr Ser Met Thr Val Met Val Phe Leu
                835                 840                 845

Met Met Leu Ser Phe Tyr Tyr Phe Ser Arg His Val Glu Lys Leu Ala
850                 855                 860

Arg Thr Leu Phe Leu Trp Lys Ile Glu Val His Asp Gln Lys Glu Arg
865                 870                 875                 880

Val Tyr Glu Met Arg Arg Trp Asn Glu Ala Leu Val Thr Asn Met Leu
                885                 890                 895

Pro Glu His Val Ala Arg His Phe Leu Gly Ser Lys Lys Arg Asp Glu
                900                 905                 910

Glu Leu Tyr Ser Gln Thr Tyr Asp Glu Ile Gly Val Met Phe Ala Ser
                915                 920                 925

Leu Pro Asn Phe Ala Asp Phe Tyr Thr Glu Glu Ser Ile Asn Asn Gly
                930                 935                 940

Gly Ile Glu Cys Leu Arg Phe Leu Asn Glu Ile Ser Asp Phe Asp
945                 950                 955                 960

Ser Leu Leu Asp Asn Pro Lys Phe Arg Val Ile Thr Lys Ile Lys Thr
                965                 970                 975

Ile Gly Ser Thr Tyr Met Ala Ala Ser Gly Val Thr Pro Asp Val Asn
                980                 985                 990

Thr Asn Gly Phe Ala Ser Ser Asn Lys Glu Asp Lys Ser Glu Arg Glu
            995                 1000                1005

Arg Trp Gln His Leu Ala Asp Leu Ala Asp Phe Ala Leu Ala Met
        1010                1015                1020
```

-continued

```
Lys Asp Thr Leu Thr Asn Ile  Asn Asn Gln Ser Phe  Asn Asn Phe
    1025            1030              1035

Met Leu Arg Ile Gly Met Asn  Lys Gly Gly Val Leu  Ala Gly Val
    1040            1045              1050

Ile Gly Ala Arg Lys Pro His  Tyr Asp Ile Trp Gly  Asn Thr Val
    1055            1060              1065

Asn Val Ala Ser Arg Met Glu  Ser Thr Gly Val Met  Gly Asn Ile
    1070            1075              1080

Gln Val Val Glu Glu Thr Gln  Val Ile Leu Arg Glu  Tyr Gly Phe
    1085            1090              1095

Arg Phe Val Arg Arg Gly Pro  Ile Phe Val Lys Gly  Lys Gly Glu
    1100            1105              1110

Leu Leu Thr Phe Phe Leu Lys  Gly Arg Asp Lys Leu  Ala Thr Phe
    1115            1120              1125

Pro Asn Gly Pro Ser Val Thr  Leu Pro His Gln Val  Val Asp Asn
    1130            1135              1140

Ser
```

BIOSENSOR FOR DETECTING SMELL, SCENT, AND TASTE

CROSS-REFERENCE TO RELATED APPLICATIONS

This application claims priority to U.S. Provisional Application Ser. No. 62/299,005, filed on Feb. 24, 2016, the disclosure of which is hereby incorporated by reference in its entirety.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "ARX007_ST25.txt", a creation date of Feb. 23, 2017, and a size of 45 kilobytes. The Sequence Listing filed via EFS-Web is part of the specification and is incorporated in its entirety by reference herein.

BACKGROUND OF THE INVENTION

The olfactory receptor genes have been characterized through homology as seven transmembrane domain G protein-coupled receptors (GPCR). It is estimated that there are probably 500-750 olfactory receptor gene sequences in humans, while there are 500-1000 olfactory genes in rat and mouse. Olfactory receptors are concentrated on the surface of the mucus coated cilia and odorant molecules bind to the olfactory receptors in the olfactory epithelium. Since mammals can detect at least 10,000 odors and there are approximately 1,000 or fewer olfactory receptors, many odorants must interact with multiple olfactory receptors.

The discriminatory power of olfactory receptors is such that it can perceive thousands of volatile chemicals as having different odors. It is known that the olfactory system uses a combinatorial receptor coding scheme to decipher the odor molecules. One olfactory receptor can recognize multiple odorants and one odorant is recognized by multiple olfactory receptors. A slight structural change in the odorant or a change in the concentration of the odorant in the environment results in a change in the odor-code of these receptors.

Each mammalian olfactory receptor neuron encodes only one olfactory receptor. The axons of the neurons expressing the same olfactory receptor converge to one olfactory bulb, which then processes the information to the brain. Olfactory receptors are structurally similar to G-Protein Coupled Receptors (GPCRs) and contain seven transmembrane (TM) domains connected by loops. The functionally important residues are present on the transmembrane helices 2-7.

Odor molecules belong to a variety of chemical classes: from alcohols, aldehydes, ketones and carboxylic acids to sulphur-containing compounds and essential oils. The physicochemical descriptors of odor molecules play an important role in the prediction of odor response by the olfactory receptor. Very identical olfactory receptor sequences can have a structural bias for ligand specificity on the basis of the number of carbon atoms present in the ligands. About 8000 odorants have been identified in food. About 400 food odorants have been characterized and this number approximately equals the number of olfactory receptors found in humans. The response of mixtures of odorants is neither the additive nor an average of its components. Some mixtures lead to the emergence of novel perceptual qualities that were not present in the individual components.

It is an object of this invention to provide a biosensor that produces an aromagraph for a mixture, composition, or molecule. It is an object of the invention to provide a biosensor that is used to deconstruct the components of a mixture, composition or molecule that are responsible for the scent, smell, odor, aroma, and/or taste of the mixture, composition or molecule. It is also an object of the invention to provide a biosensor that is used to diagnose and remediate malodors.

SUMMARY OF THE INVENTION

The invention relates to biosensors for the detection of interactions at an Olfactory Receptor. In some embodiments, the invention relates to the use of the biosensors of the invention to detect the interaction of odorants at Olfactory Receptors. In some embodiments, a plurality of biosensors are used to detect the interaction of an odorant at a plurality of Olfactory Receptors. In some embodiments, the plurality of biosensors represent the repertoire or a portion of the repertoire of an animals Olfactory Receptors. In some embodiments, the plurality of biosensors represent the repertoire or a portion of the repertoire of human Olfactory Receptors. In some embodiments, the plurality of biosensors represent the portion of the repertoire of human Olfactory Receptors that detect odorants in solution. In some embodiments, the plurality of biosensors represent the portion of the repertoire of human Olfactory Receptors that detect odorants in the gaseous phase. In some embodiments, the plurality of biosensors represent the portion of the repertoire of human Olfactory Receptors that detect a particular odorant. In some embodiments, the plurality of biosensors represent the portion of the repertoire of human Olfactory Receptors that detect a particular class or type of odorant.

In some embodiments, individual biosensors are comprised of an Olfactory Receptor that is fused in its N-terminal region to a polypeptide sequence that targets the nascent polypeptide to the host cell membrane, and fused in its C-terminal region to a polypeptide that stabilizes the receptor. In some embodiments, the polypeptide fused to the C-terminal region of the Olfactory Receptor targets the receptor to the outermembrane of the host cell. In some embodiments, the N-terminal portion of the biosensor is from positions 1-55 of the rat olfactory receptor RI7 (RI7). In some embodiments, full length olfactory receptors are used without fusing to another protein. In some embodiments, the nucleic acids encoding the RI7 portion of the fusion receptor or the full length olfactory receptor are preceded by a nucleic acid encoding an eight amino acid FLAG tag (Asp-Tyr-Lys-Asp-Asp-Asp-Asp-Lys (SEQ ID NO:1)), e.g., used for identification and purification of the olfactory receptor fusion protein. In some embodiments, the Olfactory Receptor sequences are followed by a cassette encoding Green Fluorescent Protein or Red Fluorescent protein. The GFP or RFP is fused to the olfactory receptor to allow detection of the location of the olfactory receptor when it is expressed in host cells. In some embodiments, the Olfactory Receptor is a mammalian olfactory receptor. In some embodiments, the Olfactory Receptor is a human Olfactory Receptor. In some embodiments, the human olfactory receptor is OR1A1, OR2W1, OR2J2, OR5P3, or OR6A2. In some embodiments, the ORF sequence fused in the construct comprises nucleic acids encoding the amino acids sequence of the Olfactory Receptor from amino acid position 56 to the end of the amino acid sequence.

In some embodiments, a construct is used for accepting ORF cassettes to make new biosensors of the invention. In some embodiments the ORF cassette is fused into the construct so full length human receptor protein is encoded in the construct. In some embodiments, the nucleic acid encoding the full length human olfactory receptor is fused in frame with a nucleic acid encoding an eight amino acid FLAG tag, (Asp-Tyr-Lys-Asp-Asp-Asp-Asp-Lys (SEQ ID NO:1)). In some embodiments, the Olfactory Receptor sequences are followed by a cassette encoding Green Fluorescent Protein or Red Fluorescent protein.

In some embodiments, the biosensors of the invention are also comprised of a G-protein and an adenylate cyclase. In some embodiments, the G-protein is comprised of three subunits the Gα subunit, Gβ subunit, and Gγ subunit. In some embodiments, the adenylate cyclase and the G protein are from the same species. In some embodiments, the adenylate cyclase and the G protein are from different species. In some embodiments, the G protein subunits are from the same or from different species. In some embodiments, the Olfactory Receptor, G protein and adenylate cyclase are from the same species, and in some embodiments, one or more of the components are from different species. In some embodiments, the biosensor polypeptides of the invention include polypeptides that have 70%, 80%, 90%, 95%, and 99% sequence homology with SEQ ID NO: 6-10 and 12-17.

In some embodiments, the biosensor of the invention includes a polypeptide that directly or indirectly produces a reporter molecule. In some embodiments, the biosensor of the invention includes a polypeptide that is the reporter molecule (e.g., an optical reporter). In some embodiments, the polypeptide is an adenylate cyclase. In some embodiments, the reporter molecule is cAMP. In some embodiments, the reporter(s) produced by the biosensor has a dynamic range of six to seven orders of magnitude, and the biosensor coupled to the reporter can detect binding of odorants and other molecules in a range of 0.15 parts per billion to about 420,000 parts per billion, or $10^{-9}$ M to about $10^{-3}$ M. In some embodiments, the window of detection is six to seven orders of magnitude within the range of 10 M to $10^{-12}$ M. In some embodiments, the biosensor of the invention has a dynamic range of nine to ten orders of magnitude. In some embodiments, the biosensor of the invention can detect binding of odorants and other molecules in a range of $10^{-11}$ M to about $10^{-2}$ M. In some embodiments, the window of detection is nine to ten orders of magnitude within the range of 10 M to $10^{-12}$ M. In some embodiments, the biosensor of the invention has a dynamic range of three to five orders of magnitude. In some embodiments, the window of detection is three to five orders of magnitude within the range of 10 M to $10^{-12}$ M. In some embodiments, the biosensor of the invention has a dynamic range of 1, 2, 3, 4, 5, 6, 7, 8, 9, or 10 orders of magnitude.

The invention also relates to nucleic acids encoding the biosensors of the invention. In an embodiment, the nucleic acids of the invention include nucleic acids that hybridize under stringent hybridization conditions to nucleic acids encoding one of the biosensor polypeptides of the invention. In an embodiment, the biosensor polypeptides of the invention include the polypeptides encoded by nucleic acids that hybridize under stringent hybridization conditions to nucleic acids encoding the biosensor polypeptides describe above. In an embodiment, the nucleic acids of the invention encode a polypeptide of one of SEQ ID NOS: 6-10 and 12-17, or are a nucleic acid that hybridizes under stringent hybridization conditions to a nucleic acid encoding a polypeptide of one of SEQ ID NOS: 6-10 and 12-17. In an embodiment, the nucleic acids of the invention encode a polypeptide that has 70%, 80%, 90%, 95%, and 99% sequence identity with one of SEQ ID NOS: 6-10 and 12-17.

The invention relates to the biosensor polypeptides and biosensor nucleic acids contained within host cells. In some embodiments, the host cells are eukaryotic cells. In some embodiments, the host cell is a fungal cell, animal cell, plant cell, or algae cell. In some embodiments, the fungal cell is selected from *Saccharomyces, Pichia, Aspergillus, Chrysosporium*, or *Trichoderma*. In some embodiments, the fungal cell is *Saccharomyces cerevisiae, Pichia pastoris, Aspergillus niger, Aspergillus oryzae, Chrysosporium lucknowense*, or *Trichoderma reesei*. In some embodiments, the host cell is a mammalian cell line derived from Chinese hamster cells, Human kidney cells, Monkey kidney cells, Human cervical cancer cells, or Mouse myeloma cells. In some embodiments the host cell is a human cell. In some embodiments, the host cell is a murine cell. In some embodiments, the host cell is a canine cell.

The invention also relates to the use of host cells containing the biosensor polypeptide and biosensor nucleic acids of the invention. In some embodiments, the invention relates to the use of membrane fractions with the biosensor made from host cells with the biosensor. In some embodiments, a reference receptor-reporter is included in the host cell or membrane fraction to allow relative, real-time measurements to be made on the biosensor of the invention. In some embodiments, real time measurements are used to measure the interaction of an odorant with at least one Olfactory Receptor. In some embodiments, real time measurements are used to measure the interaction of an odorant at a plurality of different Olfactory Receptors. In some embodiments, real time measurements are used to measure the interaction of a plurality of different odorants at the same or different Olfactory Receptors. In some embodiments, real time measurements are made and compared to a reference to provide comparative numbers for the interaction of an odorant at Olfactory Receptors. In some embodiments, real time measurements are made and compared to a reference to provide comparative numbers for the interaction of different odorants at the same or different Olfactory Receptors. In some embodiments, quantitating versus a reference will produce aromagraphs for molecules, mixtures, and/or compositions that can be compared and contrasted. In some embodiments, the reporter monitored in real time is an optical reporter. In some embodiments, the reporter monitored in real time is a nonoptical reporter. In some embodiments, the reference is a G-protein coupled receptor with a known affinity for a known ligand. In some embodiments, the reference receptor has an activity range of 1, 2, 3, 4, 5, 6, 7, 8, or 9 orders of magnitude. In some embodiments, the reference receptor has an activity range of 2-4 orders of magnitude and 4-5 different reference receptors are used to cover the activity range of Olfactory Receptors from 10 M to $10^{-12}$ M. In some embodiments, the reference receptor-ligand pair is selected to have an affinity that is similar to the affinity of the tested Olfactory Receptor-odorant pair. In some embodiments, the concentration of the tested odorant is varied in a series of wells over a range of 3, 4, 5, 6, 7, 8, 9, or 10 orders of magnitude and are compared to a reference. In some embodiments, the concentration of the tested odorant is varied in a series of wells over a range of 3 to 10 orders of magnitude and are compared to a reference. In some embodiments, the Olfactory Receptors are identified as having strong, intermediate, or weak interactions with the tested odorant. In some embodiments, the reference receptor is associated with a reporter that is different from the reporter associated with the Olfactory Receptor(s). In some embodiments, the different reporters are optical reporters. In some embodiments, the different optical reporters are monitored in real time in the same reaction.

In some embodiments, the biosensors of the invention are used to identify odorants in a mixture or composition that contribute to the scent, odor, smell, aroma, or taste of the mixture or composition. In some embodiments, the biosensor of the invention is used to characterize the scent, odor, smell, aroma, or taste of a composition, mixture, or a plurality of mixtures and/or compositions. In some embodiments, the biosensors are used to make a formulation or recipe for a composition or mixture that has a characteristic scent, odor, smell, aroma, or taste. In this embodiment, a component of a composition or a mixture may be replaced by a different component(s) without a loss of the characteristic scent, odor, smell, aroma, or taste by using the biosensor to find replacement component(s) that have similar interactions at the Olfactory Receptors as the replaced component. In some embodiments, the replacement component is from a natural source (replacing a non-natural component(s)). In some embodiments, the replacement component is considered to be healthy and replaces a component considered to be unhealthy. In some embodiments, the replacement component costs less. In some embodiments, the replacement component is easier to manufacture or has better properties. In some embodiments, the replacement component substitutes for an ingredient that has been banned or otherwise becomes expensive, unavailable, or hard to acquire. In some embodiments, the replacement component substitutes for two or more ingredients in the composition. In some embodiments, the composition is completely reverse engineered and a set of components that produce the composition and its characteristic scent, smell, odor, aroma, and/or taste is designed.

In some embodiments, the biosensors of the invention are used to make libraries of molecules with known aromagraphs that can be used to build or maintain designer or desired scents, odors, smells, aromas, or tastes. In some embodiments, molecules from a library with or without known aromagraphs can be used to build mixtures or compositions that mimic the aromagraphs of desired known mixtures or compositions. In some embodiments, molecules from a library can be used to build mixtures or compositions that meet an aromagraph specification. In some embodiments, the aromagraph is for a known mixture, composition or molecule. In some embodiments, the aromagraph is for a designed or theoretical scent, smell, odor, aroma, and/or taste. In some embodiments, the aromagraph is for a desired modification of a known mixture, composition, or molecule. In some embodiments, the molecules from the library can also be used to remediate malodors.

In some embodiments, the biosensors of the invention are used to standardize scents, smells, odors, aromas, and/or taste. For example, aromagraphs can be used to quantify and characterize different scents, smells, odors, aromas, and/or tastes creating a common language and description for the comparing and contrasting compositions, mixtures, and/or molecules. In some embodiments, the biosensors of the invention are used to quantify the interaction of a scent, smell, odor, aroma, and/or taste with the OR repertoire. These quantized interactions can be used to describe a scent, smell, odor, aroma, and/or taste. For example, hundreds of vanilla flavoring or vanilla extract products advertise that they provide vanilla flavor (or smell, scent, aroma). The biosensors of the invention will quantify the interaction of these vanilla products with the OR repertoire and permit standardization of these products on a functional basis. A core set of OR interactions will define the vanilla response, with many minor or side OR interactions producing the differences between these vanilla products. Standardization also allows the quantitative description of scent, smell, aroma, odor, and/or taste for purposes of branding, trademarks, and/or copyrights. Standardization also allows the quantitative description of new scents, smells, aromas, odors, and/or tastes.

In some embodiments, the biosensors of the invention are used to remediate a malodor. In this embodiment, the biosensor can be used to find a molecule(s) that can mask a malodor (e.g., from sports equipment, clothing or shoes, or products that depend on scent/smell). In some embodiments, the masking molecule binds to but does not activate (in the same way) the Olfactory Receptors which are causing the malodor scent. In this embodiment, the masking molecule can block the Olfactory Receptor(s) that perceive the malodor. In some embodiments, the masking molecule activates other Olfactory Receptors that in combination with the Olfactory Receptors activated by the malodor changes the perception of the malodor to a positive or null perception.

In some embodiments, the biosensors of the invention are used to create a composition or mixture with a desired scent, smell, odor, aroma, and/or taste. In some embodiments, the biosensors of the invention are used to make a composition or mixture that suppresses appetite. In this embodiment, the mixture or composition that suppresses appetite is placed in a device that creates an aerosol for delivering the appetite suppressant to the subject. In some embodiments, the biosensors of the invention are used to adjust the scent, smell, odor, aroma, and/or taste of a product to suit the palates of subjects in different geographic locations and/or different demographic groups. In some embodiments, a desired scent, smell, odor, and/or aroma is released from solid that contains the components for the desired scent, smell, odor, and/or aroma. In some embodiments, air freshener delivery systems are used to provide the desired scent, smell, odor, and/or aroma (e.g., glade plug-ins or other air freshener products).

In some embodiments, the biosensors of the invention are used to characterize aromascapes or odorscapes by identifying the components of an aromascape or odorscape that cause a desired perception by some subjects. In some embodiments, the biosensors of the invention are used to build aromascapes or odorscapes that produce a desired response from certain subjects. In some embodiments, certain subjects will find the aromascape or odorscape appealing, repellent, arousing, relaxing, or other desired state for producing a desired behavior. In some embodiments, the aromascape or odorscape is used to brand a product or service.

In some embodiments, the quantified scent, smell, odor, aroma, and/or taste is used to identify the scent, smell, odor, aroma, and/or taste. In some embodiments, the quantified scent, smell, odor, aroma, and/or taste is used to uniquely identify the scent, smell, odor, aroma, and/or taste. In some embodiments, the quantified scent, smell, odor, aroma, and/ or taste is used to communicate about the scent, smell, odor, aroma, and/or taste. In some embodiments, the quantified scent, smell, odor, aroma, and/or taste is used in a transaction for the scent, smell, odor, aroma, and/or taste. In some embodiments, quantified scent, smell, odor, aroma, and/or taste is used to describe a product or service. In some embodiments, quantified scent, smell, odor, aroma, and/or taste is used to market a product or service. In some embodiments, quantified scent, smell, odor, aroma, and/or taste is used to sell a product or service. In some embodiments, quantified scent, smell, odor, aroma, and/or taste is used to buy a product or service.

In some embodiments, an aromagraph is used to identify the scent, smell, odor, aroma, and/or taste. In some embodiments, an aromagraph is used to uniquely identify the scent, smell, odor, aroma, and/or taste. In some embodiments, an aromagraph is used to communicate about the scent, smell, odor, aroma, and/or taste. In some embodiments, an aromagraph is used in a transaction for the scent, smell, odor, aroma, and/or taste. In some embodiments, an aromagraph is used to describe a product or service. In some embodiments, an aromagraph is used to market a product or service. In some embodiments, an aromagraph is used to sell a product or service. In some embodiments, an aromagraph is used to buy a product or service.

BRIEF DESCRIPTION OF THE FIGURES

FIG. 1 depicts a plasmid map for some OR constructs.

DETAILED DESCRIPTION OF THE INVENTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

As used herein, an "aromagraph" refers to a digital representation of the response to an odorant by a repertoire of Olfactory Receptors.

As used herein, "aromascape" and "odorscape" are used interchangeably and both refer to the odors, aromas, smells and/or scents in the environment of a location. An aromascape or odorscape can be naturally occurring or engineered to produce a desired response(s) from an individual or group of individuals. Aromascapes or odorscapes can be areas of a place of business such as a store, hotel, or sports arena, outdoor areas such as those found in parks, sports or entertainment stadiums, As used herein, an "effective amount" refers to an amount of a compound, formulation, material, or composition, as described herein effective to achieve a particular biological result.

As used herein, the terms "express" or "expression" refer to the production of a protein product from the genetic information contained within a nucleic acid sequence.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will remain an expression vector or expression construct.

As used herein, the term "fusion protein" and "fusion polypeptide" are used interchangeably and both refer to two or more nucleotide sequences obtained from different genes that have been cloned together and that encode a single polypeptide segment. Fusion proteins are also referred to as "hybrid proteins" or "chimeric proteins." As used herein, the term "fusion protein" includes polypeptide coding segments that are obtained from different species, as well as coding segments that are obtained from the same species.

As used herein, the term "heterologous" when used with reference to portions of a polynucleotide indicates that the nucleic acid comprises two or more subsequences that are not normally found in the same relationship to each other in nature. For instance, a nucleic acid is typically recombinantly produced, having two or more sequences, e.g., from unrelated genes arranged to make a new functional nucleic acid. Similarly, a "heterologous" polypeptide or protein refers to two or more subsequences that are not found in the same relationship to each other in nature.

As used herein, the term "host cell" refers to a prokaryotic or eukaryotic cell into which the vectors of the invention may be introduced, expressed and/or propagated. A microbial host cell is a cell of a prokaryotic or eukaryotic microorganism, including bacteria, yeasts, microscopic fungi and microscopic phases in the life-cycle of fungi and slime molds. Typical prokaryotic host cells include various strains of *E. coli*. Typical eukaryotic host cells are yeast or filamentous fungi, or mammalian cells, such as Chinese hamster cells, murine NIH 3T3 fibroblasts, human kidney cells, or rodent myeloma or hybridoma cells.

As used herein, the term "isolated" refers to a nucleic acid or polypeptide separated not only from other nucleic acids or polypeptides that are present in the natural source of the nucleic acid or polypeptide, but also from other cellular components, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

As used herein, the term "mammal" refers to warm-blooded vertebrate animals all of which possess hair and suckle their young.

As used herein, the term "naturally occurring" means that the components are encoded by a single gene that was not altered by recombinant means and that pre-exists in an organism.

As used herein, an "odorant" refers to any substance that can be detected by at least one Olfactory Receptor.

As used herein, "olfaction" or "olfactory reception" refers to the detection of compounds by an Olfactory Receptor coupled to a cell signaling pathway. The compound detected is termed an "odorant" and may be air-borne (i.e., volatile) and/or in solution.

As used herein, the terms "Olfactory Receptor" or "OR" are used interchangeably herein to refer to olfactory receptors, trace amine associated receptors, vomeronasal receptors, formyl peptide receptors, membrane guanylyl cyclase, subtype GC-D receptors, and G-protein coupled taste receptors. Olfactory Receptors include hybrid receptors made from olfactory receptors, trace amine associated receptors, vomeronasal receptors, formyl peptide receptors, membrane guanylyl cyclase, subtype GC-D receptors, and G-protein coupled taste receptors.

As used herein, "percentage of sequence identity" and "percentage homology" are used interchangeably herein to refer to comparisons among polynucleotides or polypeptides, and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, *Adv Appl Math.* 2:482, 1981; by the homology alignment algorithm of Needleman and Wunsch, *J Mol Biol.* 48:443, 1970; by the search for similarity method of Pearson and Lipman, *Proc Natl Acad Sci. USA* 85:2444, 1988; by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Greene Publishing Associates, Inc. and John Wiley & Sons, Inc., (1995 Supplement). Examples of algorithms that are suitable for determining percent sequence identity and sequence similarity are the BLAST and BLAST 2.0 algorithms, which are described in Altschul et al., *J. Mol. Biol.* 215:403-410, 1990; and Altschul et al., *Nucleic Acids Res.* 25(17):3389-3402, 1977; respectively. Software for performing BLAST analyses is publicly available through the National Center for Biotechnology Information website. BLAST for nucleotide sequences can use the BLASTN program with default parameters, e.g., a wordlength (W) of 11, an expectation (E) of 10, M=5, N=−4, and a comparison of both strands. BLAST for amino acid sequences can use the BLASTP program with default parameters, e.g., a wordlength (W) of 3, an expectation (E) of 10, and the BLOSUM62 scoring matrix (see Henikoff and Henikoff, *Proc Natl Acad Sci. USA* 89:10915, 1989). Exemplary determination of sequence alignment and % sequence identity can also employ the BESTFIT or GAP programs in the GCG Wisconsin Software package (Accelrys, Madison Wis.), using default parameters provided.

As used herein, the terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, PEGylation or any other manipulation or modification, such as conjugation with a labeling or bioactive component.

As used herein, the term "purified" means that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

As used herein, the term "real time" refers to taking multiple measurements during a reaction or interaction as opposed to making a single measurement at the end of the reaction, or at a specified time point. Real time measurements are often used to quantitate the amount of a component in a sample, or to provide relative quantification of two or more components in a sample. Real time measurements can also be used to determine kinetic parameters of a reaction or interaction.

As used herein, the term "recombinant nucleic acid" refers to a nucleic acid in a form not normally found in nature. For example, a recombinant nucleic acid may be flanked by a nucleotide sequence not naturally flanking the nucleic acid or the recombinant nucleic acid may have a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it may replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

As used herein, the term "recombinant polypeptide" refers to a polypeptide expressed from a recombinant nucleic acid, or a polypeptide that is chemically synthesized in vitro.

As used herein, the term "recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

As used herein, the terms "repertoire" or "library" refers to a library of genes encoding a plurality of different Olfactory Receptors. In some embodiments, the repertoire or library represents all of the Olfactory Receptors of a species, e.g., human, dog, or cat. In some embodiments, the repertoire or library represents the Olfactory Receptors that detect a taste, scent, smell, aroma, and/or odor. In some embodiments, the repertoire or library represents the Olfactory Receptors that detect a desired, pleasing, arousing, or adverse taste, scent, smell, aroma, and/or odor. In some embodiments, the repertoire or library represents the Olfactory Receptors of a class, family, or type.

As used herein, the term "reporter" or "reporter molecule" refers to a moiety capable of being detected indirectly or directly. Reporters include, without limitation, a chromophore, a fluorophore, a fluorescent protein, a luminescent protein, a receptor, a hapten, an enzyme, and a radioisotope.

As used herein, the term "reporter gene" refers to a polynucleotide that encodes a reporter molecule that can be detected, either directly or indirectly. Exemplary reporter genes encode, among others, enzymes, fluorescent proteins, bioluminescent proteins, receptors, antigenic epitopes, and transporters.

As used herein, "stringent hybridization conditions" refers to hybridizing in 50% formamide at 5×SSC at a temperature of 42° C. and washing the filters in 0.2×SSC at 60° C. (1×SSC is 0.15M NaCl, 0.015M sodium citrate.) Stringent hybridization conditions also encompasses low ionic strength and high temperature for washing, for example 0.015 M sodium chloride/0.0015 M sodium citrate/0.1% sodium dodecyl sulfate at 50° C.; hybridization with a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, "substantial identity" refers to a polynucleotide or polypeptide sequence that has at least 80 percent sequence identity, at least 85 percent identity and 89 to 95 percent sequence identity. Substantial identity also encompasses at least 99 percent sequence identity as compared to a reference sequence over a comparison window of at least 20 residue positions or a window of at least 30-50 residues, wherein the percentage of sequence identity is calculated by comparing the reference sequence to a sequence that includes deletions or additions or substitutions over the window of comparison. In specific embodiments applied to polypeptides, the term "substantial identity" means that two polypeptide sequences, when optimally aligned, such as by the programs GAP or BESTFIT using standard parameters, i.e., default parameters, share at least 80 percent sequence identity, preferably at least 89 percent sequence identity, at least 95 percent sequence identity or more (e.g., 99 percent sequence identity).

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, "taste receptors" refers to G-protein coupled taste receptors for detecting sweet, bitter, and umami (glutamate), and ion channels and ionotropic receptors for detecting salty and sour.

As used herein, "transfected" or "transformed" or "transduced" are defined to be a process by which an exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

The singular terms "a", "an", and "the" include plural referents unless context clearly indicates otherwise. Similarly, the word "or" is intended to include "and" unless the context clearly indicates otherwise. Numerical limitations given with respect to concentrations or levels of a substance, such as an antigen, are intended to be approximate. Thus, where a concentration is indicated to be at least (for example) 200 µg, it is intended that the concentration be understood to be at least approximately "about" or "about" 200 µg.

Olfactory Receptors

Most Olfactory Receptors are G-protein coupled receptors that associate with a G-protein for signal transduction after the receptor is activated by an odorant. GPCRs have a conserved structural feature of seven α-helical transmembrane regions. Most olfactory receptors are about 320±25 amino acids in length. The differences in length mostly result from variations in the N-terminal and C-terminal regions. Most olfactory receptors include the motif MAYDRYVAIC (SEQ ID NO:2) located at the junction of TM3 (transmembrane section 3) and the intracellular loop between TM3 and TM4. Other motifs conserved in some of the olfactory receptors, include, for example, LHTPMY (SEQ ID NO:3) within the first intracellular loop, FSTCSSH (SEQ ID NO:4) at the beginning of TM6, and PMLNPF (SEQ ID NO:5) in TM7.

In some embodiments, the olfactory receptors used in the invention are human olfactory receptors, or olfactory receptors from another mammal, or olfactory receptors from another organism. In some embodiments, olfactory receptors used in the invention are hybrid olfactory receptors. In some embodiments, amino acids from the N-terminal region of one olfactory receptor are fused to the N-terminal region of a second, different olfactory receptor. In some embodiments, the N-terminal amino acids are from amino acid positions 1-61 of the donor olfactory receptor. In some embodiments, the N-terminal amino acids are from amino acid positions 1-55 of the donor olfactory receptor. In some embodiments, the N-terminal amino acids are from amino acid positions 1-20 or the amino acids up to the first transmembrane domain, or amino acid positions 1-40 which includes the consensus sequence of the first transmembrane domain. In some embodiments, the N-terminal amino acids are fused to the acceptor olfactory receptor at its N-terminal region of amino acid positions 1-61. In some embodiments, amino acids from the C-terminus of a donor polypeptide are fused to the C-terminal end of the acceptor olfactory receptor. In some embodiments, 1-50 amino acids from the C-terminus of the acceptor olfactory receptor are replaced by amino acids from a donor polypeptide. In some embodiments, 1-55 amino acids from the C-terminus of the acceptor olfactory receptor are replaced by amino acids from a donor polypeptide. In some embodiments, the donor polypeptide is an olfactory receptor.

In some embodiments, the acceptor olfactory receptor is a human olfactory receptor and the donor olfactory receptor is a human olfactory receptor. In some embodiments, the acceptor olfactory receptor is a human olfactory receptor and the donor olfactory receptor is a murine olfactory receptor. In some embodiments, the acceptor olfactory receptor is a human olfactory receptor and the donor olfactory receptor is a yeast polypeptide. In some embodiments, the acceptor olfactory receptor is a murine olfactory receptor and the donor olfactory receptor is a murine olfactory receptor. In some embodiments, the acceptor olfactory receptor is a murine olfactory receptor and the donor olfactory receptor is a human olfactory receptor. In some embodiments, the acceptor olfactory receptor is a murine olfactory receptor and the donor olfactory receptor is a yeast polypeptide. In some embodiments, the acceptor olfactory receptor is a canine olfactory receptor and the donor olfactory receptor is a canine olfactory receptor. In some embodiments, the acceptor olfactory receptor is a canine olfactory receptor and the donor olfactory receptor is a human or a murine olfactory receptor. In some embodiments, the acceptor olfactory receptor is a canine olfactory receptor and the donor olfactory receptor is a yeast polypeptide.

In some embodiments, the amino acids added from the donor olfactory receptor replace the corresponding amino acid positions in the acceptor olfactory receptor. In some embodiments, the added amino acids from the donor olfactory receptor increase the total number of amino acids in the acceptor olfactory receptor. In some embodiments, the acceptor olfactory receptor has fewer amino acids (than the starting acceptor olfactory receptor) after the fusion is made.

Most mammalian olfactory receptors can be classified into two phylogenetic groups, class I and class II olfactory receptors. Class I olfactory receptors are similar to fish olfactory receptors and class II receptors are most characteristic of mammals. In mammals a majority of the olfactory receptors are in class II, but mammals also have class I receptors, for example, humans and mice each have more than 100 class I olfactory receptors. The number of olfactory genes varies among mammals from about 800 (including pseudogenes) in primates to about 1,500 in dogs and mice. The number of functional olfactory receptors varies from about 262 in platypus and 390 in humans to 1,284 in rats and 1,194 in mice.

The repertoire of human olfactory receptors includes about 850 genes and pseudogenes, including about 390 putatively functional genes, in 18 gene families, and 300 subfamilies. Databases setting out the organization of the human olfactory receptor genes into families and subfamilies, along with links to the polypeptide and nucleic acid sequences of the olfactory receptors can be found at HUGO Gene Nomenclature Committee website, genenames.org/genefamilies/OR, the Olfactory Receptors Database at senselab.med.yale.edu/ORDB/info/humanorseqanal, and HORDE, the Human Olfactory Data Explorer, found at genome.weizmann.ac.il/horde/, all of which are incorporated by reference in their entirety for all purposes.

The repertoire of mouse olfactory receptors includes about 1,296 genes and pseudogenes, of which about 80% are putatively functional, in 228 families. Databases with the organization of the mouse olfactory receptor genes into families and subfamilies, along with links to the polypeptide and nucleic acid sequences of the olfactory receptors can be found at the Olfactory Receptors Database at senselab.med.yale.edu/ORDB/info/humanorseqanal, which is incorporated by reference in its entirety for all purposes.

The repertoire of canine olfactory receptors includes about 1,094 genes. Quignon et al., Genome Biol. vol. 6, pp. R83-R83.9 (2005); Olender et al., Genomics vol. 83, pp. 361-372 (2004); Quignon et al., Chapter 13, CSH Monographs Volume 44: The Dog and Its Genome (2006); which are incorporated by reference in their entirety for all purposes.

The Olfactory Receptor repertoires of other mammals are also within the scope of the invention, including, for example, the Olfactory Receptor repertoires of mice, rats, cats, cows and cattle, horses, goats, pigs, and bears.

In some embodiments, a biosensor is made from human olfactory receptor 1A1 having the amino acid sequence (OR1A1, NCBI 9606, UP000005640, HGNC 8179, NP 055380.2, DMDM 212276451):

```
                                                   (SEQ ID NO: 6)
MRENNQSSTL EFILLGVTGQ QEQEDFFYIL FLFIYPITLI

GNLLIVLAIC SDVRLHNPMY FLLANLSLVD IFFSSVTIPK

MLANHLLGSK SISFGGCLTQ MYFMIALGNT DSYILAAMAY

DRAVAISRPL HYTTIMSPRS CIWLIAGSWV IGNANALPHT

LLTASLSFCG NQEVANFYCD ITPLLKLSCS DIHFHVKMMY

LGVGIFSVPL LCIIVSYIRV FSTVFQVPST KGVLKAFSTC

GSHLTVVSLY YGTVMGTYFR PLTNYSLKDA VITVMYTAVT

PMLNPFIYSL RNRDMKAALR KLFNKRISS
```

In some embodiments, N-terminal amino acids of the human olfactory receptor 1A1 are replaced with N-terminal amino acids from the human olfactory receptor 6A2 having the sequence (OR6A2, NCBI 9606, UP000005640, HGNC 15301; NP 003687.2)

```
                                                   (SEQ ID NO: 7)
MEWRNHSGRV SEFVLLGFPA PAPLQVLLFA LLLLAYVLVL

TENTLIIMAI RNHSTLHKPM YFFLANMSFL EIWYVTVTIP

KMLAGFVGSK QDHGQLISFE GCMTQLYFFL GLGCTECVLL

AVMAYDRYMA ICYPLHYPVI VSGRLCVQMA AGSWAGGFGI

SMVKVFLISG LSYCGPNIIN HFFCDVSPLL NLSCTDMSTA

ELTDFILAIF ILLGPLSVTG ASYVAITGAV MHIPSAAGRY

KAFSTCASHL TVVIIFYAAS IFIYARPKAL SAFDTNKLVS

VLYAVIVPLL NPIIYCLRNQ EVKRALCCTL HLYQHQDPDP

KKASRNV
```

In some embodiments, amino acids from the N-terminal region of OR6A2 (amino acid positions 1-61) are fused to OR1A1 to make a fusion olfactory receptor to be used in the biosensor. In some embodiments, at least 20 contiguous amino acids from the N-terminal region of OR6A2 are fused to with OR1A1. In some embodiments, the N-terminal region of OR6A2 is amino acid positions 1-55. These amino acids of OR6A2 are fused at a position in the N-terminal region of OR1A1, ranging from 1-61. In some embodiments, the N-terminal sequence from OR6A2 is fused to amino acid position 56 of OR1A1. In some embodiments, the human OR6A2 is used in the biosensor without modification. In some embodiments, the human OR6A2 receptor is modified at its C-terminal end by fusing with other C-terminal sequences from other olfactory receptors. In some embodiments, the human OR6A2 is modified at its N-terminal end by fusing N-terminal sequences from other olfactory receptors.

In some embodiments, a biosensor is made from the human olfactory receptor 2J2 (OR2J2, HGNC 8260; NP_112167).

```
                                         (SEQ ID NO: 8)
MMIKKNASSE  DFFILLGFSN  WPQLEVVLFV  VILIFYLMTL

TGNLFIIILS  YVDSHLHTPM  YFFLSNLSFL  DLCYTTSSIP

QLLVNLRGPE  KTISYAGCMV  QLYFVLALGI  TECVLLVVMS

YDRYVAVCRP  LHYTVLMHPR  FCHLLVAASW  VIGFTISALH

SSFTFWVPLC  GHRLVDHFFC  EVPALLRLSC  VDTHANELTL

MVMSSIFVLI  PLILILTTYG  AIARAVLSMQ  STTGLQKVFR

TCGAHLMVVS  LFFIPVMCMY  LQPPSENSPD  QGKFIALFYT

VVTPSLNPLI  YTLRNKHVKG  AAKRLLGWEW  GK
```

In some embodiments, a biosensor is made from the human olfactory receptor 2W1 (OR2W1, HGNC 8281; NP_112165).

```
                                         (SEQ ID NO: 9)
MDQSNYSSLH  GFILLGFSNH  PKMEMILSGV  VAIFYLITLV

GNTAIILASL  LDSQLHTPMY  FFLRNLSFLD  LCFTTSIIPQ

MLVNLWGPDK  TISYVGCIIQ  LYVYMWLGSV  ECLLLAVMSY

DRFTAICKPL  HYFVVMNPHL  CLKMIIMIWS  ISLANSVVLC

TLTLNLPTCG  NNILDHFLCE  LPALVKIACV  DTTTVEMSVF

ALGIIIVLTP  LILILISYGY  IAKAVLRTKS  KASQRKAMNT

CGSHLTVVSM  FYGTIIYMYL  QPGNRASKDQ  GKFLTLFYTV

ITPSLNPLIY  TLRNKDMKDA  LKKLMRFHHK  STKIKRNCKS
```

In some embodiments, a biosensor is made from the human olfactory receptor 5P3 (OR5P3, HGNC 14784; NP_703146).

```
                                         (SEQ ID NO: 10)
MGTGNDTTVV  EFTLLGLSED  TTVCAILFLV  FLGIYVVTLM

GNISIIVLIR  RSHHLHTPMY  IFLCHLAFVD  IGYSSSVTPV

MLMSFLRKET  SLPVAGCVAQ  LCSVVTFGTA  ECFLLAAMAY

DRYVAICSPL  LYSTCMSPGV  CIILVGMSYL  GGCVNAWTFI

GCLLRLSFCG  PNKVNHFFCD  YSPLLKLACS  HDFTFEIIPA

ISSGSIIVAT  VCVIAISYIY  ILITILKMHS  TKGRHKAFST

CTSHLTAVTL  FYGTITFIYV  MPKSSYSTDQ  NKVVSVFYTV

VIPMLNPLIY  SLRNKEIKGA  LKRELRIKIF  S
```

In some embodiments, N-terminal amino acids from the rat RI7 olfactory receptor are fused to the N-terminal end of a human olfactory receptor. The rat RI7 olfactory receptor has the N-terminal sequence:

```
                                         (SEQ ID NO: 11)
MERRNHSGRV  SEFVLLGFPA  PAPLRVLLFF  LSLLAYVLVL

TENMLIIIAI  RNHPTLHKPM  YFFLANMSFL  EIWYVTVTIP

KMLAGFIGSK  ENHGQLISFE
```

In some embodiments, amino acid positions 1-55 of the N-terminal sequence of the rat RI7 olfactory receptor are fused to the N-terminal end of the human olfactory receptor.

In some embodiments, the Olfactory Receptor is fused at its N- or C-terminal end with FLAG or HIS tags to assist in certain purification and biochemical characterizations of the biosensor polypeptides.

Human olfactory receptors are classified into 18 families: 1, 2, 3, 4, 5, 6, 7, 8, 9, 10, 11, 12, 13, 14, 51, 52, 55 and 56. Family OR1 has 21 members: OR1A, OR1B, OR1C, OR1D, OR1E, OR1F, OR1G, OR1H, OR1I, OR1J, OR1K, OR1L, OR1M, OR1N, OR1P, OR1Q, OR1R, OR1S, OR1X, OR1AA, and OR1AB. Family OR2 has 41 members: OR2A, OR2B, OR2C, OR2D, OR2E, OR2F, OR2G, OR2H, OR21, OR2J, OR2K, OR2L, OR2M, OR2N, OR2Q, OR2R, OR2S, OR2T, OR2U, OR2V, OR2W, OR2X, OR2Y, OR2Z, OR2AD, OR2AE, OR2AF, OR2AG, OR2AH, OR2AI, OR2AJ, OR2AK, OR2AL, OR2AM, OR2AO, OR2AP, OR2AS, and OR2AT. Family OR3 has 3 members: OR3A, OR3B, and OR3D. Family OR4 has 21 members: OR4A, OR4B, OR4C, OR4D, OR4E, OR4F, OR4G, OR4H, OR4K, OR4L, OR4M, OR4N, OR4P, OR4Q, OR4R, OR4S, OR4T, OR4U, OR4V, OR4W, and OR4X. Family OR5 has 49 members: OR5A, OR5B, OR5C, OR5D, OR5E, OR5F, OR5G, OR5H, OR5I, OR5J, OR5K, OR5L, OR5M, OR5P, OR5R, OR5S, OR5T, OR5V, OR5W, OR5AC, OR5AH, OR5AK, OR5AL, OR5AM, OR5AN, OR5AO, OR5AP, OR5AQ, OR5AR, OR5AS, OR5AU, OR5W, OR5X, OR5Y, OR5Z, OR5BA, OR5BB, OR5BC, OR5BD, OR5BE, OR5BH, OR5BJ, OR5BK, OR5BL, OR5BM, OR5BN, OR5BP, OR5BQ, OR5BR, OR5BS, and OR5BT. Family OR6 has 21 members: OR6A, OR6B, OR6C, OR6D, OR6E, OR6F, OR6J, OR6K, OR6L, OR6M, OR6N, OR6P, OR6Q, OR6R, OR6S, OR6T, OR6U, OR6V, OR6W, OR6X, and OR6Y. Family OR7 has 9 members: OR7A, OR7C, OR7D, OR7E, OR7G, OR7H, OR7K, OR7L, and OR7M. Family OR8 has 18 members: OR8A, OR8B, OR8C, OR8D, OR8F, OR8G, OR8H, OR8I, OR8J, OR8K, OR8L, OR8Q, OR8R, OR8S, OR8T, OR8U, OR8V, and OR8X. Family OR9 has 12 members: OR9A, OR9G, OR9H, OR9J, OR9K, OR9L, OR9M, OR9N, OR9P, OR9Q, OR9R, and OR9S. Family OR10 has 29 members: OR10A, OR10B, OR10C, OR10D, OR10G, OR10H, OR10J, OR10K, OR10N, OR10P, OR10Q, OR10R, OR10S, OR10T, OR10U, OR10V, OR10W, OR10X, OR10Y, OR10Z, OR10AA, OR10AB, OR10AC, OR10AD, OR10AE, OR10AF, OR10AG, OR10AH, and OR10AK. Family OR11 has 11 members: OR11A, OR11G, OR11H, OR11I, OR11J, OR11K, OR11L, OR11M, OR11N, OR11P, OR11Q. Family OR12 has 1 member: OR12D. Family OR13 has 11 members: OR13A, OR13C, OR13D, OR13E, OR13F, OR13G, OR13H, OR131, OR13J, OR13K, and OR13Z. Family OR14 has 6 members: OR14A, OR14C, OR141, OR14J, OR14K, and OR14L. Family OR51 has 21 members: OR51A, OR51B, OR51C, OR51D, OR51E, OR51F, OR51G, OR51H, OR51I, OR51J, OR51K, OR51L, OR51M, OR51N, OR51P, OR51Q, OR51R, OR51S, OR51T, OR51V, and OR51AB. Family OR52 has 22 members: OR52A, OR52B, OR52D, OR52E, OR52H, OR52I, OR52J, OR52K, OR52L, OR52M, OR52N, OR52P, OR52Q, OR52R, OR52S, OR52T, OR52U, OR52V, OR52W, OR52X, OR52Y, and OR52Z. Family OR55 has 1 member: OR55B. Family OR56 has 2 members: OR56A and OR56B.

Biosensors

The invention relates to biosensors for the detection of interactions at an Olfactory Receptor. In some embodiments, the biosensors are used to detect the interaction of an odorant at an Olfactory Receptor. In some embodiments, a biosensor comprises a plurality of Olfactory Receptors and the plurality of Olfactory Receptors are used to detect an odorant. In some embodiments, the plurality of Olfactory Receptors in the biosensor represent the repertoire or a portion of the repertoire of an animals Olfactory Receptors. In some embodiments, the plurality of Olfactory Receptors in the biosensor represents the repertoire or a portion of the repertoire of human Olfactory Receptors. In some embodiments, the plurality of Olfactory Receptors in the biosensor represents the portion of the repertoire of human Olfactory Receptors that detect odorants in solution. In some embodiments, the plurality of Olfactory Receptors in the biosensor represents the portion of the repertoire of human Olfactory Receptors that detect odorants in the gaseous phase. In some embodiments, the plurality of Olfactory Receptors in the biosensor represents the portion of the repertoire of human Olfactory Receptors that produce a pleasurable or positive response. In some embodiments, the plurality of Olfactory Receptors in the biosensor represents the portion of the repertoire of human Olfactory Receptors that produce an adverse or negative response. In some embodiments, the plurality of Olfactory Receptors in the biosensor represents the portion of the repertoire of human Olfactory Receptors from one of the 18 families of human Olfactory Receptors.

In some embodiments, individual biosensors are comprised of an Olfactory Receptor that is fused in its N-terminal region to a polypeptide sequence that targets the nascent polypeptide to the host cell secretory apparatus for insertion of the Olfactory Receptor into the membrane, and fused in its C-terminal region to a polypeptide that stabilizes the receptor in the membrane. In some embodiments, the polypeptide fused to the C-terminal region of the Olfactory Receptor targets the receptor to the outermembrane of the host cell. In some embodiments, the Olfactory Receptor is a mammalian olfactory receptor. In some embodiments, the Olfactory Receptor is a human Olfactory Receptor. In some embodiments, a full length Olfactory Receptor is used in the biosensor. In some embodiments, the full length Olfactory Receptor is a human Olfactory Receptor.

In some embodiments, the biosensor includes a G-protein signaling pathway. Many G-protein signaling pathways may be used. In some embodiments, the G-protein signaling pathway comprises the G-protein-mediated activation of adenylate cyclase with resultant production of cAMP as a second messenger. In some embodiments, the cAMP interacts with a cAMP activated cation channel.

In some embodiments, the biosensors of the invention are also comprised of a G-protein and an adenylate cyclase (e.g., Uniprot O60266). In some embodiments, the G-protein is comprised of three subunits the Gα subunit (e.g., Uniprot P38405), Gβ subunit (e.g., Uniprot P62879) and Gγ subunit (e.g., Uniprot P63218). In some embodiments, the adenylate cyclase and the G protein are from the same species. In some embodiments, the adenylate cyclase and the G protein are from different species. In some embodiments, the G protein subunits from the same or from different species. In some embodiments, the Olfactory Receptor, G protein and adenylate cyclase are from the same species, and in some embodiments, one or more of the components are from different species. In some embodiments, the Olfactory Receptor and G protein of the biosensor originate from human polypeptides. In some embodiments, the biosensor polypeptides of the invention include polypeptides that have 70%, 80%, 90%, 95%, and 99% sequence homology with SEQ ID NO: 6-10 and 12-17, or one of the human OR receptors from the 18 human OR gene families.

In some embodiments, the biosensor includes a reporter. In some embodiments, the G proteins of the biosensor interact directly with a reporter polypeptide to produce a detectable signal, e.g., adenylate cyclase is a reporter polypeptide that produces cAMP. The cAMP molecule itself can be detected (e.g., commercially available kits are sold by, for example, Thermofisher Scientific, Ray Biotech, Enzo Life Sciences, Cayman Chemical, and Cell BioLabs). In some embodiments, the G proteins of the biosensor interact with a polypeptide that induces a reporter. In some embodiments, the G proteins interact with a polypeptide (e.g., adenylate cyclase) to create a first signal, and a second system amplifies the first signal when the reporter responds to the first signal. In some embodiments, multiple amplification steps are used to increase detection of interactions at the Olfactory Receptor. In some embodiments, both the primary signal and the amplified or multiple amplified signals are detected so as to increase the dynamic range of binding interactions detected by the biosensor.

In some embodiments, the biosensor includes one or more reporters. In some embodiments, a heterologous gene encoding a reporter protein is introduced into the host cell such that the host cell expresses the reporter, and the biosensor activates the reporter when an appropriate interaction occurs at the Olfactory Receptor of the biosensor. In some embodiments, the host cells are engineered to express a single reporter. In some embodiments, different host cells, each expressing a different reporter, are used to enhance signal detection of the biosensor. In some embodiments, the host cell is engineered to express two or more reporter products, for example by using a single vector construct encoding two or more reporters. In some embodiments, the reporter or reporters provide a dynamic range of detection over at least 3, 4, 5, 6, 7, 8, 9, or 10 orders of magnitude, covering a range of detection at Olfactory Receptors in the range of from about $10^{-12}$M to about 10 M.

In some embodiments, the reporter or reporters are one or more of a fluorescent reporter, a bioluminescent reporter, an enzyme, and an ion channel. Examples of fluorescent reporters include, for example, green fluorescent protein from *Aequorea victoria* or *Renilla reniformis*, and active variants thereof (e.g., blue fluorescent protein, yellow fluorescent protein, cyan fluorescent protein, etc.); fluorescent proteins from Hydroid jellyfishes, Copepod, Ctenophora, Anthrozoas, and Entacmaea quadricolor, and active variants thereof; and phycobiliproteins and active variants thereof. Other fluorescent reporters include, for example, small molecules such as CPSD (Disodium 3-(4-methoxyspiro {1,2-dioxetane-3,2'-(5'-chloro)tricyclo [3.3.1.1$^{3,7}$]decan}-4-yl) phenyl phosphate, ThermoFisher Catalog #T2141). Bioluminescent reporters include, for example, aequorin (and other $Ca^{+2}$ regulated photoproteins), luciferase based on luciferin substrate, luciferase based on Coelenterazine substrate (e.g., *Renilla, Gaussia,* and *Metridina*), and luciferase from *Cypridina*, and active variants thereof. In some embodiments, the bioluminescent reporter include, for example, North American firefly luciferase, Japanese firefly luciferase, Italian firefly luciferase, East European firefly luciferase, Pennsylvania firefly luciferase, Click beetle luciferase, railroad worm luciferase, *Renilla* luciferase, *Gaussia* luciferase, *Cypridina* luciferase, *Metrida* luciferase, OLuc, and red firefly luciferase, all of which are commercially available from ThermoFisher Scientific and/or Promega. Enzyme reporters include, for example, β-galactosidase, chloramphenicol acetyltransferase, horseradish peroxidase, alkaline phosphatase, acetylcholinesterase, and catalase. Ion channel reporters, include, for example, cAMP activated cation channels. The reporter or reporters may also include a Positron Emission Tomography (PET) reporter, a Single Photon Emission Computed Tomography (SPECT) reporter, a photoacoustic reporter, an X-ray reporter, and an ultrasound reporter.

In some embodiments, antibodies are used to amplify the signal from the Olfactory Receptor binding interaction. In some embodiments, the reporter is a polypeptide or small molecule detectable by an antibody. In some embodiments, the small molecule or polypeptide is detected in an ELISA. In some embodiments, an antibody sandwich assay is used to amplify the signal from the small molecule or polypeptide reporter.

In some embodiments, real time measurements are made with the biosensor of the invention. In some embodiments, the reporter emits light or produces a molecule that can be detected with an optical sensor. In these embodiments, real time measurements can be obtained from the biosensor by recording the change in light emission over time as the biosensor interacts with a potential ligand. The real time measurements can be used to quantify the binding interaction by an absolute measurement or a relative measurement. In the absolute measurement, the real time signal is compared to a standard to determine the binding activity at the Olfactory Receptor. In some embodiments, known amounts of ligand to an Olfactory Receptor are used to generate a standard binding curve for receptor occupancy versus reporter gene output. Binding of a test ligand can then be compared to the standard curve to quantify interaction of the test ligand at the Olfactory Receptor. In the relative measurement, the biosensor includes internal references that allow differences in interactions at an Olfactory Receptor to be compared. In some embodiments, a reference G protein coupled receptor is included in the host cell, and a known amount of the reference ligand is added to the reference receptor to act as a standard. In some embodiments, the reference receptor is coupled to a different reporter, e.g, a reporter polypeptide that provides a different optical signal from the Olfactory Receptor reporter. In some embodiments, the reference and test receptors are coupled to different fluorescent protein such as green fluorescent protein, GFP, and red fluorescent protein, RFP. The ratio of green fluorescence to red fluorescence could be compared for different test ligands at the same Olfactory Receptor, or to compare binding of the same test ligand to different Olfactory Receptors.

In some embodiments, real time data is obtained from a biosensor with a non-optical reporter. In some embodiments, the signal from a first reporter system is amplified by a second reporter system so as to increase the signal from weak interactions at an Olfactory Receptor. In some embodiments, the GTP/GDP ratio of the biosensor is controlled to regulate the sensitivity of the G-protein coupled signal transduction from the receptor. In some embodiments, the GTP/GDP ratio is controlled to alter the dynamic range of the biosensor.

The product of the reporter gene can be detected by any appropriate detection method and apparatus, depending on the type of reporter product expressed from the reporter gene. By way of example, an exemplary reporter gene encodes a light producing protein (e.g., luciferase or eGFP), and this phenotype can be detected using optical imaging. In the descriptions herein, expression of a reporter is meant to include expression of the corresponding reporter gene resulting in expression of the encoded reporter or reporter molecule.

In an embodiment, the polypeptides of the invention include polypeptides encoded by nucleic acids that hybridize under stringent hybridization conditions to nucleic acids encoding one of the polypeptides of SEQ ID NOS: 6-10 and 12-17, or encoding one of the human OR receptors from the 18 families of human olfactory receptors. In an embodiment, the polypeptides of the invention include polypeptides encoded by nucleic acids that hybridize under stringent hybridization conditions to nucleic acids encoding one of the polypeptides of SEQ ID NOS: 6-10 and 12-17, or a nucleic acid encoding one of the human OR receptors from the 18 families of human olfactory receptors. In an embodiment, the polypeptides of the invention include polypeptides encoded by nucleic acids that hybridize under stringent hybridization conditions to nucleic acids encoding the polypeptide of SEQ ID NO: 6 or 7.

In an embodiment, the polypeptides of the invention have at least 70%, 80%, 90%, 95%, or 99% sequence identity to one of SEQ ID NOS: 6-10 and 12-17, or one of the human OR receptors from the 18 families of human olfactory receptors. In an embodiment, the polypeptides of the invention have at least 70%, 80%, 90%, 95%, or 99% sequence identity to one of SEQ ID NOS: 6-7. In an embodiment, the EphA3 polypeptides of the invention have at least 70%, 80%, 90%, 95%, or 99% sequence identity to SEQ ID NO: 6.

In some embodiments, the threshold of detection of human Olfactory Receptors in the biosensors of the invention are from about 0.15 parts per billion to about 420,000 parts per billion or over a range of 6-7 orders of magnitude. In some embodiments, the range of detection of human Olfactory Receptors in the biosensors of the invention are from about $10^{-9}$ M to about $10^{-3}$ M or over a range of about 6 orders of magnitude. In some embodiments, the range of detection is over 3, 4, 5, 6, 7, 8, 9, or 10 orders of magnitude in the range of ligand from 10 M to $10^{-12}$ M.

The polypeptides of the invention encompass fragments and variants of the polypeptides of the invention. Thus, the term "fragment or variant polypeptide" further contemplates deletions, additions and substitutions to the sequence, so long as the polypeptide functions as described herein. The term "conservative variation" denotes the replacement of an amino acid residue by another biologically similar residue, or the replacement of a nucleotide in a nucleic acid sequence such that the encoded amino acid residue does not change or is changed to another structurally, chemically or otherwise functionally similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, and tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

"Variant" polypeptides or nucleic acids of the invention encompass polypeptides or nucleic acids with substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they possess the ability to elicit an immune response.

Homologs of polypeptides of the invention from other alleles are intended to be within the scope of the present invention. As used herein, the term "homologs" includes analogs and paralogs. The term "anologs" refers to two polynucleotides or polypeptides that have the same or similar function, but that have evolved separately in unrelated host organisms. The term "paralogs" refers to two polynucleotides or polypeptides that are related by duplication within a genome. Paralogs usually have different functions, but these functions may be related. Analogs and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type polypeptide or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of the gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide that is immunoreactive with the wild-type polypeptide. These variants or derivatives include polypeptides having minor modifications of the polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein. The term "variant" also includes the modification of a polypeptide where the native signal peptide is replaced with a heterologous signal peptide to facilitate the expression or secretion of the polypeptide from a host species. The term "variant" may also include 'mimitopes', which are completely different protein sequence but similar structure, that also induce cross-reactive immunity.

Polypeptides of the invention also may include amino acid sequences for introducing a glycosylation site or other site for modification or derivatization of the polypeptide. In an embodiment, the polypeptides of the invention described above may include the amino acid sequence N-X-S or N-X-T that can act as a glycosylation site. During glycosylation, an oligosaccharide chain is attached to asparagine (N) occurring in the tripeptide sequence N-X-S or N-X-T, where X can be any amino acid except Pro. This sequence is called a glycosylation sequence. This glycosylation site may be placed at the N-terminus, C-terminus, or within the internal sequence of the polypeptide.

Host Cells

In the present invention, various eukaryotic cells can be used as the host cell. In some embodiments, the host cell is a fungal cell, animal cell, plant cell, or algae cell. In some embodiments, the eukaryotic cells are fungi cells, including, but not limited to, fungi of the genera *Aspergillus, Trichoderma, Saccharomyces, Chrysosporium, Klyuveromyces, Candida, Pichia, Debaromyces, Hansenula, Yarrowia, Zygosaccharomyces, Schizosaccharomyces, Penicillium,* or *Rhizopus*. In some embodiments, the fungi cells are *Saccharomyces cerevisiae, Pichia pastoris, Aspergillus niger, Aspergillus oryzae, Chrysosporium lucknowense,* or *Trichoderma reesei*.

In some embodiments, the host cells of the invention are animal cells. In some embodiments, the host cells are cells from a commercially valuable livestock. In some embodiments, the animal cells are mammalian cells, such as that of bovine, canine, feline, hamster, mouse, porcine, rabbit, rat, or sheep. In some embodiments, the mammalian cells are cells of primates, including but not limited to, monkeys, chimpanzees, gorillas, and humans. In some embodiments, the mammalians cells are mouse cells, as mice routinely function as a model for other mammals, most particularly for humans (see, e.g., Hanna, J. et al., "Treatment of sickle cell anemia mouse model with iPS cells generated from autologous skin," Science 318:1920-23, 2007; Holtzman, D. M. et al., "Expression of human apolipoprotein E reduces amyloid-β deposition in a mouse model of Alzheimer's disease," J Clin Invest. 103(6):R15-R21, 1999; Warren, R. S. et al., "Regulation by vascular endothelial growth factor of human colon cancer tumorigenesis in a mouse model of experimental liver metastasis," J Clin Invest. 95: 1789-1797, 1995; each publication incorporated herein by reference). Animal cells include, for example, fibroblasts, epithelial cells (e.g., renal, mammary, prostate, lung), keratinocytes, hepatocytes, adipocytes, endothelial cells, hematopoietic cells. In some embodiments, the animal cells are adult cells (e.g., terminally differentiated, dividing or non-dividing) or stem cells. In some embodiments, mammalian cell lines are used as host cells of the invention. In some embodiments, the cell lines are derived from Chinese hamster cells, Human kidney cells, Monkey kidney cells, Human cervical cancer cells, or Mouse myeloma cells. These and other mammalian cell lines are well known in the art, for example, the mammalian cell lines publicly available from ThermoFisher Scientific, ATCC (American Type Culture Collection), and Charles River Laboratories International, Inc. The cell lines disclosed at the web-sites for ThermoFisher, ATCC, and Charles River Laboratories are incorporate by reference in their entirety for all purposes.

In some embodiments the eukaryotic cells are plant cells. In some embodiments the plant cells are cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, eucalyptus, hemp, lettuce, lentil, maize, mango, melon, oat, papaya, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), Arabidopsis, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

In some embodiments, the eukaryotic cells are algal, including but not limited to algae of the genera *Chlorella, Chlamydomonas, Scenedesmus, Isochrysis, Dunaliella, Tetraselmis, Nannochloropsis*, or *Prototheca*, Nucleic Acids In some embodiments, the present invention relates to the nucleic acids that encode, at least in part, the individual peptides, polypeptides, and proteins of the present invention. In some embodiments, the nucleic acids may be natural, synthetic or a combination thereof. The nucleic acids of the invention may be RNA, mRNA, DNA, cDNA, or synthetic nucleic acids.

In some embodiments, the nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells. In some embodiments, the vector is related to the autonomously replicating plasmids in yeast YRp, YEp, and YCp. All three are *S. cerevisiae/E. coli* shuttle vectors that typically carry a multiple cloning site (MCS) for the insertion of expression cassettes. In some embodiments, the yeast epitope tagging vectors, pESC are used. The pESC vectors are commercially available from Agilent Technologies.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In some embodiments, an exemplary selection scheme utilizes a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art. Examples of yeast selection genes, include, URA3, TRP1, LEU2, HIS3, LYS2, ADE2, MET15, hphNT1, and natNT2. Da Silva et al., FEMS Yeast Research 12:197-214 (2012), which is incorporated by reference in its entirety for all purposes. In some embodiments, these yeast selection genes are used with appropriate auxotrophic yeast strains.

Inducible promoters are also contemplated as part of the invention. Examples of inducible promoters include, but are not limited to yeast promoters for GAL1, GAL7, and GAL10 (galactose-inducible) CUP1 (copper ion inducible), ADH2 (glucose repression), and mammalian promoters such as a metallothionein promoter, a glucocorticoid promoter, a progesterone promoter, a c-fos promoter, the T-REx system of ThermoFisher which places expression from the human cytomegalovirus immediate-early promoter under the control of tetracycline operator(s), and RheoSwitch promoters of Intrexon. Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), Da Silva et al., FEMS Yeast Research 12:197-214 (2012); U.S. Pat. Nos. 8,895,306, 8,822,754, 8,748,125, 8,536,354, all of which are incorporated by reference in their entirety for all purposes.

Expression vectors of the invention typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

The nucleic acid of the present invention can be operably linked to another nucleic acid so as to be expressed under control of a suitable promoter. The nucleic acid of the present invention can be also operably linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

In some embodiments, it may be desirable to modify the polypeptides of the present invention. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, Gene 8:81-97, 1979; Roberts et al., *Nature* 328:731-734, 1987, which is incorporated by reference in its entirety for all purposes). In some embodiments, the recombinant nucleic acids encoding the polypeptides of the invention are modified to provide preferred codons which enhance translation of the nucleic acid in a selected organism.

The polynucleotides of the invention also include polynucleotides including nucleotide sequences that are substantially equivalent to the polynucleotides of the invention. Polynucleotides according to the invention can have at least about 80%, more typically at least about 90%, and even more typically at least about 95%, sequence identity to a polynucleotide of the invention. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants in accordance with this invention (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., *Angew Chem Intl Ed.* 28:716-34, 1989 (which is incorporated by reference in its entirety for all purposes), may also be used to prepare such nucleic acids.

In some embodiments, amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, or degradation/turnover rate.

Alternatively, where alteration of function is desired, insertions, deletions or non-conservative alterations can be engineered to produce altered polypeptides or chimeric polypeptides. Such alterations can, for example, alter one or more of the biological functions or biochemical characteristics of the polypeptides of the invention. For example, such alterations may change polypeptide characteristics such as ligand-binding affinities or degradation/turnover rate. Further, such alterations can be selected so as to generate polypeptides that are better suited for expression, scale up and the like in the host cells chosen for expression.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art, and this technique is exemplified by publications such as, Edelman et al., *DNA* 2:183 (1983). A versatile and efficient method for producing site-specific changes in a polynucleotide sequence is described in Zoller and Smith, *Nucleic Acids Res.* 10:6487-6500 (1982).

PCR may also be used to create amino acid sequence variants of the nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the target at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985), and other mutagenesis techniques well known in the art, such as, for example, the techniques in Sambrook et al., supra, and Ausubel et al., supra.

Process for Making Host Cells with Biosensors

As described above, Olfactory Receptors are genetically engineered for expression in a desired host cell. The Olfactory Receptors may be from a certain species, or maybe fusion or hybrid constructs. The N-terminal and C-terminal sequences of the Olfactory Receptor or fusion/hybrid localize the Olfactory Receptor or fusion/hybrid to the host cell membrane, and if appropriate to the outer membrane of a host cell. These Olfactory Receptor or fusion/hybrid gene constructs are placed into appropriate expression vectors for the host cell and then these expression constructs or expression vectors are placed inside a host cell.

In some embodiments, the host cells are also genetically engineered to express human G protein subunits. In some embodiments, the host cells are also genetically engineered to express the human G protein subunits G$\alpha$, G$\beta$, and G$\gamma$. In this embodiment, the genes encoding the human G$\alpha$, G$\beta$, and G$\gamma$ subunits are placed under the control of appropriate control sequences (promoters, enhancers, translation start sequences, polyA sites, etc.) for the desired host cell, and these constructs for the human G$\alpha$, G$\beta$, and G$\gamma$ subunits are placed into the desired host cell. In some embodiments, the human G protein is also associated with adenylate cyclase. In this embodiment, the gene for an appropriate adenylate cyclase is placed under the control of appropriate control sequences for the desired host cell, and this construct is placed into the desired host cell.

In the process of the present invention, a eukaryotic host cell as describe above is used. In some embodiments, a fungal cell is used. In some embodiments, the fungal cell is from the *Aspergillus, Trichoderma, Saccharomyces, Chrysosporium, Kluyveromyces, Candida, Pichia, Debaromyces, Hansenula, Yarrowia, Zygosaccharomyces, Schizosaccharomyces, Penicillium,* or *Rhizopus* genera. In some embodiments, the fungal cell is a *Saccharomyces cerevisiae*. In some embodiments, a eukaryotic cell derived from a mammal, for example, a human cell, or a cell derived from a non-human mammal such as a monkey, a mouse, a rat, a pig, a horse, or a dog can be used. The cell used in the process of the present invention is not particularly limited, and any cell can be used.

In some embodiments, the nucleic acid encoding the biosensor is introduced to the host cell by transfection (e.g., Gorman, et al. Proc. Natl. Acad. Sci. 79.22 (1982): 6777-6781, which is incorporated by reference in its entirety for all purposes), transduction (e.g., Cepko and Pear (2001) Current Protocols in Molecular Biology unit 9.9; DOI: 10.1002/0471142727.mb0909s36, which is incorporated by reference in its entirety for all purposes), calcium phosphate transformation (e.g., Kingston, Chen and Okayama (2001) Current Protocols in Molecular Biology Appendix 1C; DOI: 10.1002/0471142301.nsa01cs01, which is incorporated by reference in its entirety for all purposes), cell-penetrating peptides (e.g., Copolovici, Langel, Eriste, and Langel (2014) ACS Nano 2014 8 (3), 1972-1994; DOI: 10.1021/nn4057269, which is incorporated by reference in its entirety for all purposes), electroporation (e.g Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of these references are incorporated by reference in their entirety for all purposes), microinjection (e.g., McNeil (2001) Current Protocols in Cell Biology unit 20.1; DOI: 10.1002/0471143030.cb2001s18, which is incorporated by reference in its entirety for all purposes), liposome or cell fusion (e.g., Hawley-Nelson and Ciccarone (2001) Current Protocols in Neuroscience Appendix 1F; DOI: 10.1002/0471142301.nsa01fs10, which is incorporated by reference in its entirety for all purposes), mechanical manipulation (e.g. Sharon et al. (2013) PNAS 2013 110(6); DOI: 10.1073/pnas.1218705110, which is incorporated by reference in its entirety for all purposes) or other well-known technique for delivery of nucleic acids to eukaryotic cells. Once introduced, the nucleic acid can be transiently expressed episomally, or can be integrated into the genome of the eukaryotic cell using well known techniques such as recombination (e.g., Lisby and Rothstein (2015) Cold Spring Harb Perspect Biol. March 2; 7(3). pii: a016535. doi: 10.1101/cshperspect.a016535, which is incorporated by reference in its entirety for all purposes), or non-homologous integration (e.g., Deyle and Russell (2009) Curr Opin Mol Ther. 2009 August; 11(4):442-7, which is incorporated by reference in its entirety for all purposes). The efficiency of homologous and non-homologous recombination can be facilitated by genome editing technologies that introduce targeted double-stranded breaks (DSB). Examples of DSB-generating technologies are CRISPR/Cas9, TALEN, Zinc-Finger Nuclease, or equivalent systems (e.g., Cong et al. Science 339.6121 (2013): 819-823, Li et al. *Nucl. Acids Res* (2011): gkr188, Gajet al. Trends in Biotechnology 31.7 (2013): 397-405, all of which are incorporated by reference in their entirety for all purposes), transposons such as Sleeping Beauty (e.g., Singh et al (2014) Immunol Rev. 2014 January; 257(1):181-90. doi: 10.1111/imr.12137, which is incorporated by reference in its entirety for all purposes), targeted recombination using, for example, FLP recombinase (e.g., O'Gorman, Fox and Wahl Science (1991) 15:251(4999):1351-1355, which is incorporated by reference in its entirety for all purposes), CRE-LOX (e.g., Sauer and Henderson PNAS (1988): 85; 5166-5170), or equivalent systems, or other techniques known in the art for integrating the nucleic acid into the eukaryotic cell genome.

In an embodiment, the nucleic acid(s) encoding the G$\alpha$, G$\beta$, G$\gamma$, adenylate cyclase, and the Olfactory Receptor are integrated into the eukaryotic host cell chromosome at a genomic safe harbor site, such as, for example, the CCR5, AAVS1, human ROSA26, or PSIP1 loci for human cells. (Sadelain et al., Nature Rev. 12:51-58 (2012); Fadel et al., J. Virol. 88(17):9704-9717 (2014); Ye et al., PNAS 111(26): 9591-9596 (2014), all of which are incorporated by reference in their entirety for all purposes.) Safe harbor sites for yeast cells, e.g., *Saccharomyces cerevisiae*, include, for example, yeast Ty $\delta$ sequences. In an embodiment, the host cell is a human cell and the integration of the nucleic acid(s) encoding the G$\alpha$, G$\beta$, G$\gamma$, adenylate cyclase, and the Olfactory Receptor at the CCR5 and/or PSIP1 locus is done using a gene editing system, such as, for example, CRISPR, TALEN, or Zinc-Finger nuclease systems. In an embodiment, the eukaryotic cell is a *Saccharomyces cerevisiae* cell and a CRISPR system is used to integrate the Gα, Gβ, Gγ, adenylate cyclase, and the Olfactory Receptor at Ty δ locus. In an embodiment, integration of the nucleic acid at safe harbor loci using the CRISPR system also deletes a portion, or all, of the safe harbor loci. In an embodiment, Cas9 in the eukaryotic cell may be derived from a plasmid encoding Cas9, an exogenous mRNA encoding Cas9, or recombinant Cas9 polypeptide alone or in a ribonucleoprotein complex. (Kim et al (2014) Genome 1012-19. doi:10.1101/gr.171322.113; Wang et al (2013) Cell 153 (4). Elsevier Inc.: 910-18. doi:10.1016/j.cell.2013.04.025, both of which are incorporated by reference in their entirety for all purposes.)

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

Uses of Biosensors

In some embodiments, the nucleic acids encoding the components of the biosensor (e.g., the Olfactory Receptor, G-proteins, and adenylate cyclase and/or other reporter) are placed in a suitable host cell (e.g., *Saccharomyces cerevisiae*) and the host cells with the biosensor are used for detection of odorants. In some embodiments, the host cells are lysed and a membrane fraction is obtained that includes the Olfactory Receptor, G-proteins, and adenylate cyclase (and/or other reporter). In this embodiment, the membrane fraction is used as the biosensor for detection of odorants.

In some embodiments, the biosensors of the invention are used to identify the Olfactory Receptors that interact with a mixture, composition, or molecule and the degree of interaction at each Olfactory Receptor by the mixture, composition, or molecule. The identity of Olfactory Receptors and the degree of interaction produces an aromagraph for a mixture, composition, or molecule. In some embodiments, the biosensors of the invention are used to deconstruct the aromagraph of a mixture, composition, and/or molecule to identify which components or substituents of the mixture, composition, or molecule produce the aromagraph. In some embodiments, the aromagraph of a mixture is deconstructed by removing components from the mixture and testing the component minus mixture on the biosensor. Removed components that contribute to the aromagraph will be identified by changes in the aromagraph. Similarly, a composition can be deconstructed by removing components and identifying changes to the aromagraph. In some embodiments, the removed component is also tested on the biosensors to characterize the aromagraph for the component. In some embodiments, the substituents on a molecule are changed in effort to identify which substituents of the molecule interact with the Olfactory Receptor(s).

In some embodiments, aromagraphs are used to create a specification for a mixture, composition, and/or molecule. This aromagraph specification can be used for QC and QA of a product. In some embodiments, the product for QC or QA includes, for example, a spice, seasoning, fragrance, perfume, food product, pet product. In some embodiments, aromagraph specifications are used for the ingredients of a product. In this embodiment, an ingredient can be exchanged for a different ingredient or for the same ingredient from a different source as long as the aromagraph specification is met. In some embodiments, a new ingredient or the same ingredient from a different source will require slight modification (e.g., addition of molecules) to meet the aromagraph specification. The use of the biosensors of the invention and aromagraphs allows for rationale design and rationale substitution in the creation and maintenance of products that rely upon aroma, scent, smell, odor, and/or taste. In some embodiments, the aromagraph for a product or composition is used to replace an ingredient in the product or composition that has become unavailable, expensive, or hard to acquire. In some embodiments, the aromagraph is used to replace a non-healthy ingredient with a healthy ingredient. In some embodiments, the aromagraph is used to replace a non-natural ingredient with a natural ingredient. In some embodiments, the aromagraph is used to replace an ingredient with a less costly ingredient. In some embodiments, the aromagraph is used to replace a plurality of ingredients with fewer ingredients. In some embodiments, the product or composition is a flavor or fragrance, and the aromagraph of the flavor or fragrance is used to build a substitute recipe for the flavor or fragrance. The invention also relates to the new products made by these new formulations.

In some embodiments, the biosensors of the invention are used to standardize scents, smells, aromas, odors, and/or taste. In some embodiments, aromagraphs are used to standardize scent, smell, aroma, odor, and/or a taste. In some embodiments, the biosensors of the invention are used to quantify the interaction of a scent, smell, odor, aroma, and/or taste with the OR repertoire. These quantized interactions can be used to describe a scent, smell, odor, aroma, and/or taste. For example, hundreds of vanilla flavoring or vanilla extract products advertise that they provide vanilla flavor (or smell, scent, aroma). The biosensors of the invention can quantify the interaction of these vanilla products with the OR repertoire and permit standardization of these products on a functional basis. A core set of OR interactions will define the vanilla response, with many minor or side OR interactions producing the differences between these vanilla products. Standardization also allows the quantitative description of scent, smell, aroma, odor, and/or taste for purposes of branding, trademarks, and/or copyrights. Standardization also allows the quantitative description of new scents, smells, aromas, odors, and/or tastes. In some embodiments, the elements of flavor wheels are digitized into Aromagraphs and qualitative terms from the flavor wheel are associated with quantified interactions at Olfactory Receptors. See Google Images for Flavor Wheels. For example, the flavor wheel descriptors caramel (honey, butterscotch, butter, soy sauce, chocolate, molasses), chemical (Sulphur dioxide, ethanol, acetic acid, ethyl acetate, wet wool, wet dog, Sulphur dioxide, burnt match, cabbage, skunk, garlic, mercaptan, hydrogen sulfide, rubbery, diesel, kerosene, plastic, tar), earthy (moldy, moldy cork, mushroom, dusty), floral (geranium, violet, rose, orange blossom), fruity (grapefruit, lemon, blackberry, raspberry, strawberry, black currant, cherry, apricot, peach, apple, pineapple, melon, banana, strawberry jam, raisin, prune, fig, methyl anthranilate), herbaceous or vegetative (cut green grass, bell pepper, eucalyptus, mint, green beans, asparagus, green olive, black olive, artichoke, hay, straw, tea, tobacco), microbiological (mousey, horsey, yoghurt, sweaty, sauerkraut, leesy, baker's yeast, nutty (walnut, hazelnut, almond), oxidized (sherry), pungent (menthol, alcohol), spic (licorice anise, black pepper, cloves), and woody (smokey, burnt toast, coffee, medicinal, phenolic, bacon, oak, cedar, vanilla) are quantified by their Olfactory Receptor responses.

In some embodiments, the quantified scent, smell, odor, aroma, and/or taste is used to identify the scent, smell, odor, aroma, and/or taste. In some embodiments, the quantified scent, smell, odor, aroma, and/or taste is used to uniquely identify the scent, smell, odor, aroma, and/or taste. In some embodiments, the quantified scent, smell, odor, aroma, and/or taste is used to communicate about the scent, smell, odor, aroma, and/or taste. In some embodiments, the quantified scent, smell, odor, aroma, and/or taste is used in a transaction for the scent, smell, odor, aroma, and/or taste. In some embodiments, quantified scent, smell, odor, aroma, and/or taste is used to describe a product or service. In some embodiments, quantified scent, smell, odor, aroma, and/or taste is used to market a product or service. In some embodiments, quantified scent, smell, odor, aroma, and/or taste is used to sell a product or service. In some embodiments, quantified scent, smell, odor, aroma, and/or taste is used to buy a product or service.

In some embodiments, an aromagraph is used to identify the scent, smell, odor, aroma, and/or taste. In some embodiments, an aromagraph is used to uniquely identify the scent, smell, odor, aroma, and/or taste. In some embodiments, an aromagraph is used to communicate about the scent, smell, odor, aroma, and/or taste. In some embodiments, an aromagraph is used in a transaction for the scent, smell, odor, aroma, and/or taste. In some embodiments, an aromagraph is used to describe a product or service. In some embodiments, an aromagraph is used to market a product or service. In some embodiments, an aromagraph is used to sell a product or service. In some embodiments, an aromagraph is used to buy a product or service.

In some embodiments, the biosensors of the invention are used to remediate a malodor. In some embodiments, the malodor arises in the manufacture of a product that has a characteristic scent, smell, aroma, odor, and/or taste. The lot of product with the malodor can be tested on the biosensors of the invention and the aromagraph obtained compared to the aromagraph specification for the product. This will identify new or changed Olfactory Receptor interactions causing the malodor. In some embodiments, this malodor is remediated by deconstructing the product with the malodor to identify which component is causing the malodor. In some embodiments, the malodor is caused by new interactions at new Olfactory Receptors. In this embodiment, the malodor could be remediated by adding an inhibitor(s) that blocks the new Olfactory Receptor(s) from being activated. Alternatively, a molecule could be added that activates other Olfactory Receptors which combined with the new Olfactory Receptor stimulation turns the perception of the malodor into a pleasant, minor, or not perceived smell, scent, aroma, odor, and/or taste. In some embodiments, the malodor is caused by an imbalance in components that changes the interactions at the Olfactory Receptors in the aromagraph specification. In this embodiment, the malodor may be removed by balancing the components of the product to restore the aromagraph specification of the product. In some embodiments, the aromagraph may be balanced by increasing the amount of certain ingredients to rationally balance the aromagraph to the product specification based on the aromagraphs of the ingredients. In some embodiments, the aromagraph may be balanced by adding molecules known to stimulate or inhibit certain Olfactory Receptors so as to bring the aromagraph of the product with the malodor back into balance with its aromagraph specification.

In some embodiments, the malodor is associated with sports equipment, clothing, or shoes. The malodor can be characterized on the biosensors of the invention to create a malodor aromagraph. In some embodiments, the malodor is remediated by adding an inhibitor(s) that blocks Olfactory Receptor(s) in the malodor aromagraph from being activated. Alternatively, a molecule could be added that activates other Olfactory Receptors which combined with the Olfactory Receptors stimulated by the malodor turns the perception of the malodor into a pleasant, minor, or not perceived smell, scent, aroma, odor, and/or taste.

In some embodiments, the biosensors of the invention are used to make a mixture, composition, or molecule with a desired aromagraph specification. For example, the biosensors of the invention can be used to deconstruct the aromagraph for cadaverine and/or putrescine. These compounds are known to cause avoidance behavior in some subjects. Deconstructing the contribution of certain moieties to the cadaverine and putrescine aromagraphs may identify the Olfactory Receptors responsible for the avoidance behavior of these molecules. Rationale design can then be used to make a mixture, composition, or molecule that can stimulate these Olfactory Receptors to cause the avoidance behavior without the foul smell of cadaverine or putrescine. Such a rationally designed aroma, scent, smell or odor could be used in an aerosol to cause avoidance behavior and suppress appetite in subjects. Alternatively, the rationally designed aroma, scent, smell or odor could be used to keep subjects away from an area as the avoidance behavior caused by these Olfactory Receptors would cause subjects to avoid the scent, smell, aroma, and/or odor.

In some embodiments, the rationally designed aroma, scent, smell, odor, and/or taste is reverse engineered from a known aroma, scent, smell, odor, and/or taste. This reverse engineering can produce a new formulation for making the known aroma, scent, smell, odor, and/or taste. In some embodiments, the rationally designed aroma, scent, smell, odor, and/or taste includes, for example, new car smell, perfumes, fragrances, or flavors. In some embodiments, the perfume or fragrance is archived in the Osmothèque. In some embodiments, an aromagraph for an archived fragrance or perfume from the Osmothèque is used to create new formulation and recipe for making the fragrance or perfume. In some embodiments, the recipe for the fragrance or perfume from the Osmothèque has been lost, and the biosensors and aromagraphs of the invention are used to create a recipe and formulation for making the fragrance or perfume.

In some embodiments, the rationally designed aroma, scent, smell and/or odor is delivered to an environment by placing it in a material (plastic, leather, cloth, wood, wax, etc.) from which the aroma, scent, smell and/or odor is slowly released over time. In some embodiments, the aroma, scent, smell and/or odor is released from the material when it is subjected to a different set of conditions. For example, the aroma, scent, smell and/or odor could be placed in a material where it is released upon heating of the material (e.g., similar to glad plug-ins). Other changes in conditions besides temperature can also be used to release the aroma, scent, smell and/or odor, including, for example, a solvent, pH, airflow, light, etc. can be used to release the aroma, scent, smell and/or odor from the material.

In some embodiments, aromagraph specifications are designed to account for differences in socioeconomic, cultural, geographic, or the palates of other groupings of certain subjects. In some embodiments, aromagraph specifications are created for aromascapes or odorscapes that produce a desired response or state in a subject from certain socioeconomic, cultural, geographic, and/or other groupings. In some embodiments, the aromascape specification is designed to relax, attract, repel, etc. subjects from certain socioeconomic, cultural, geographic, and/or other groups. In some embodiments, aromagraph specification are created for products so subjects in certain socioeconomic, cultural, geographic, and/or other groupings will have a desired response to the product. In some embodiments, aromagraph specifications are created or defined as part of product or service branding.

In some embodiments, the biosensors and aromagraphs of the invention are used to tailor a product for the palates of consumers in different geographic locations. In some embodiments, a products aroma, scent, smell, odor, and/or taste can be designed to be appealing to consumers in different geographic locations. In some embodiments, aromagraphs for a class or group of products from different cultures and/or geographic locations can be used to tailor new products of the class or group for different geographic/cultural markets. For example, a chocolate product can be designed for Middle Eastern or Indian markets by using aromagraphs for similar types of products from these geographic areas to identify OR interactions that are favored by consumers for those types of products. Using this information on OR receptors and aromagraphs, a chocolate product can be rationally designed for these different markets.

In some embodiments, the biosensors of the invention are used to detect and diagnose disease. Many diseases are associated with odors or smells that can be used to diagnose the disease. For example, certain lung, liver, kidney and digestive diseases can be detected from a patient's breath, diabetes, schizophrenia, Parkinson's, and certain infectious diseases (tuberculosis and typhoid) can be detected by a patient's odor, and some cancers can be detected by the olfactory repertoire of canines. In some embodiments, odors, scent, and/or smell associated with a patient's skin, sweat, hair, saliva, and other body secretions (e.g., ear wax) can be associated with disease diagnosis. In some embodiments, a biosensor of the invention is used to create aromagraphs of patient's with diseases that can be detected by odor, scent, and/or smell. In some embodiments, the aromagraph is based on a human repertoire of Olfactory Receptors. In some embodiments, the aromagraph is based on a canine repertoire of Olfactory Receptors. In some embodiments, the aromagraph is based on a mouse or rat repertoire of Olfactory Receptors. In some embodiments, the aromagraph is based on a mammalian repertoire of Olfactory Receptors. Patients can then be diagnosed for disease by taking odor, breath or other samples and screening them to see whether the aromagraph for a certain disease is detected.

In some embodiments, the biosensors of the invention are used to identify sets of OR that are associated with disease. In some embodiments, panels of ligands for these disease specific OR(s) are made and can be used to monitor a disease by the changes in a patient's response at the OR associated with the disease. For example, a poor sense of smell is one of the early warning signs of Alzheimer's. The degradation of the sense of smell is associated with both a loss of the ability of the brain to sense some OR and the loss of Olfactory Receptor memory (association of a smell with the stimulation of certain OR). The loss of OR response and OR memory can be used as an early warning sign for Alzheimer's, and can also be used to monitor response to anti-Alzheimer's treatment, as the loss of smell is reversible in some cases. In some embodiments, patients at risk for Alzheimer's can be tested for loss of smell at disease associated ORs, and for OR memory. In some embodiments, patients who reach a certain age can be screened for loss of smell at disease associated ORs and for OR memory. In some embodiments, panels of odorants can be used to monitor a patient's sense of smell at the disease associated ORs. In some embodiments, the panel of odorants have different interactions at the disease associated OR from strong to weak interactions. In some embodiments, the biosensor of the invention can be used to identify disease associated ORs and to identify ligands that can be used to diagnose early Alzheimer's.

In some embodiments, the biosensors of the invention are used in drug discovery. In some embodiments, the biosensors of the invention are used to design the taste, smell, odor, scent, and/or aroma of a drug and/or pharmaceutical composition. In some embodiments, the biosensors of the invention are used to identify and mask a taste, smell, odor, scent, and/or aroma associated with a drug and/or pharmaceutical composition. In some embodiments, the taste, smell, odor, scent, and/or aroma which is masked produces a negative response in certain subjects. In some embodiments, the taste, smell, odor, scent, and/or aroma which is masked produces a positive or addictive response in certain subjects. In some embodiments, the biosensors of the invention are used to design abuse-deterrent formulations. In some embodiments, the adversant formulations are used for opioid drugs including, for example, hydrocodone (Vicodin), oxycodone (OxyContin, Percocet, Roxicodone, Oxecta), morphine (Kadian, Avinza), codeine, buprenorphine (Buprenex, Butrans), butorphanol (Stadol), hydromorphone (Dilaudid, Hydrostat, Exalgo), levorphanol (Levo-Dromoran), meperidine (Demerol), methadone (Dolophine, Methadose), nalbuphine (Nubain), oxymorphone (Numorphan), pentazocine (Talwin), propoxyphene (Cotanal-65, Darvon), fentanyl (Sublimaze, Actiq, Durogesic, Fentora, Matrifen, Hadid, Onsolis, Instanyl, Abstral, Lazanda), tramadol (Ultram), and tapentadol (Nucynta). In some embodiments, an adversant is included in the formulation that produces a taste, smell, odor, scent, and/or aroma that produces an avoidance behavior or other strongly negative reaction by subjects. In some embodiments, the adversant is comprised of two or more components that when sensed together produce the negative reaction, but when sensed individually do not induce the negative reaction. In some embodiments, the two components can be engineered in the abuse deterrent formulation to be released at different times, but when the formulation is crushed or extracted to abuse the drug, this releases both components to form the adversant. In some embodiments, the adversant formed when the two components combine becomes a gas at room temperature, or becomes a gas after the components mix and the drug formulation is heated.

In some embodiments, an adversant is designed for application to products. In some embodiments, the adversant is applied to products, including, for example, tobacco or marijuana. In these embodiments, the adversant would be formulated to adsorb into the plant tissues so it is released along when the tobacco or marijuana is used, for example, the adversant could be designed to be released when the tobacco or marijuana is burned. In some embodiments, the adversant is one that alters the interaction of the product with the OR of the subject resulting in an adverse aroma, scent, smell, odor, and/or taste.

In some embodiments, the biosensors of the invention are used to identify panels of odorants for groups of ORs. In some embodiments, a panel of odorants is used to monitor an individual's sense of smell and/or taste. In some embodiments, a panel of odorants is used to monitor the sense of smell and/or taste in a group of individuals, e.g., a panel of individuals for testing smells and/or tastes of products. In some embodiments, the panel of odorants is used to set a baseline for an individual. In some embodiments, the panel of odorants is used to set a specification for a tasting/smelling panel of individuals. In some embodiments, the specification is used to set a panel of individuals for each tasting/smelling panel study.

In some embodiments, the biosensor of the invention is used to identify the components of a taste, smell, odor, scent, and/or aroma so that components of various tastes, smells, odors, scents, and/or aromas are released together or sequentially to produce desired effects at desired times. In some embodiments, a series of components are released so that at a first time period, the components produce a taste, smell, odor, scent, and/or aroma that produces desired response in the first time period, and then another or different group of components is released at a second time period to change or introduce a new taste, smell, odor, scent, and/or aroma to produce a different desired response in the second time period. This changing of a taste, smell, odor, scent, and/or aroma in different time periods can be repeated for as many time periods as desired.

In some embodiments, the invention relates to panels or libraries of odorants with known Aromagraphs generated from the biosensors of the invention. These panels or libraries of odorants can be mixed and matched to make a composition that will have a desired Aromagraph. In some embodiments, a device contains the panel or library of odorants and can make compositions that will meet a specific Aromagraph by mixing odorants from the panel or library. In some embodiments, the device generates an Aromagraph from a composition, and makes a composition that matches the Aromagraph of the tested composition. In some embodiments, the device makes the composition matching the Aromagraph of the tested composition at a site remote from where the testing of the composition occurs. In some embodiments, the device makes the composition matching the Aromagraph of the tested composition at a site remote from where the desired Aromagraph is inputted.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

EXAMPLES

Example 1: Making a Biosensor in a Yeast Cell

The N-terminal 55 amino acids of the human OR6A2 receptor are fused to the N-terminal region of the human OR1A1 receptor in place of the N-terminal 55 amino acids of OR1A1 to give a biosensor Olfactory Receptor with the sequence:

```
                                          (SEQ ID NO: 12)
MEWRNHSGRV SEFVLLGFPA PAPLQVLLFA LLLLAYVLVL

TENTLIIMAI RNHSTHNPMY FLLANLSLVD IFFSSVTIPK

MLANHLLGSK SISFGGCLTQ MYFMIALGNT DSYILAAMAY
```

-continued
```
DRAVAISRPL HYTTIMSPRS CIWLIAGSWV IGNANALPHT

LLTASLSFCG NQEVANFYCD ITPLLKLSCS DIHFHVKMMY

LGVGIFSVPL LCIIVSYIRV FSTVFQVPST KGVLKAFSTC

GSHLTVVSLY YGTVMGTYFR PLTNYSLKDA VITVMYTAVT

PMLNPFIYSL RNRDMKAALR KLFNKRISS
```

A nucleic acid encoding this Olfactory Receptor is engineered into a yeast cell that has been previously engineered to express the human G protein subunits Gα, Gβ, and Gγ, and adenylate cyclase. Yeast were engineered with constructs that placed the human Gα, Gβ, and Gγ subunits:

```
                                          (SEQ ID NO: 13)
MGCLGGNSKTTEDQGVDEKERREANKKIEKQLQKERLAYKATHRLLLLGA

GESGKSTIVKQMRILHVNGFNPEEKKQKILDIRKNVKDAIVTIVSAMSTI

IPPVPLANPENQFRSDYIKSIAPITDFEYSQEFFDHVKKLWDDEGVKACF

ERSNEYQLIDCAQYFLERIDSVSLVDYTPTDQDLLRCRVLTSGIFETRFQ

VDKVNFHMFDVGGQRDERRKWIQCFNDVTAIIYVAACSSYNMVIREDNNT

NRLRESLDLFESIWNNRWLRTISIILFLNKQDMLAEKVLAGKSKIEDYFP

EYANYTVPEDATPDAGEDPKVTRAKFFIRDLFLRISTATGDGKHYCYPHF

TCAVDTENIRRVFNDCRDIIQRMHLKQYELL (SEQ ID NO: 14)
MSELEQLRQEAEQLRNQIRDARKACGDSTLTQITAGLDPVGRIQMRTRRT

LRGHLAKIYAMHWGTDSRLLVSASQDGKLIIWDSYTTNKVHAIPLRSSWV

MTCAYAPSGNFVACGGLDNICSIYSLKTREGNVRVSRELPGHTGYLSCCR

FLDDNQIITSSGDTTCALWDIETGQQTVGFAGHSGDVMSLSLAPDGRTFV

SGACDASIKLWDVRDSMCRQTFIGHESDINAVAFFPNGYAFTTGSDDATC

RLFDLRADQELLMYSHDNIICGITSVAFSRSGRLLLAGYDDFNCNIWDAM

KGDRAGVLAGHDNRVSCLGVTDDGMAVATGSWDSFLKIWN (SEQ ID NO: 15)
MSGSSSVAAMKKVVQQLRLEAGLNRVKVSQAAADLKQFCLQNAQHDPLLT

GVSSSTNPFRPQKVCSFL
``` under the control of either the yeast GAL1 or GAL10 promoter. The yeast strain was also engineered to express human adenylate cyclase (human adenylate cyclase type 5, NP 001186571.1):

```
                                          (SEQ ID NO: 16)
MPRNQGFSEPEYSAEYSAEYSVSLPSDPDRGVGRTHEISVRNSGSCLCLP

RFMRLTFVPESLENLYQTYFKRQRHETLLVLVVFAALFDCYVVVMCAVVF

SSDKLASLAVAGIGLVLDIILFVLCKKGLLPDRVTRRVLPYVLWLLITAQ

IFSYLGLNFARAHAASDTVGWQVFFVFSFFITLPLSLSPIVIISVVSCVV

HTLVLGVTVAQQQQEELKGMQLLREILANVFLYLCAIAVGIMSYYMADRK

HRKAFLEARQSLEVKMNLEEQSQQQENLMLSILPKHVADEMLKDMKKDES

QKDQQQFNTMYMYRHENVSILFADIVGFTQLSSACSAQELVKLLNELFAR

FDKLAAKYHQLRIKILGDCYYCICGLPDYREDHAVCSILMGLAMVEAISY

VREKTKTGVDMRVGVHTGTVLGGVLGQKRWQYDVWSTDVTVANKMEAGGI
```

-continued
PGRVHISQSTMDCLKGEFDVEPGDGGSRCDYLEEKGIETYLIIASKPEVK

KTATQNGLNGSALPNGAPASSKSSSPALIETKEPNGSAHSSGSTSEKPEE

QDAQADNPSFPNPRRRLRLQDLADRVVDASEDEHELNQLLNEALLERESA

QVVKKRNTFLLSMRFMDPEMETRYSVEKEKQSGAAFSCSCVVLLCTALVE

ILIDPWLMTNYVTFMVGEILLLILTICSLAAIFPRAFPKKLVAFSTWIDR

TRWARNTWAMLAIFILVMANVVDMLSCLQYYTGPSNATAGMETEGSCLEN

PKYYNYVAVLSLIATIMLVQVSHMVKLTLMLLVAGAVATINLYAWRPVFD

EYDHKRFREHDLPMVALEQMQGFNPGLNGTDRLPLVPSKYSMTVMVFLMM

LSFYYFSRHVEKLARTLFLWKIEVHDQKERVYEMRRWNEALVTNMLPEHV

ARHFLGSKKRDEELYSQTYDEIGVMFASLPNFADFYTEESINNGGIECLR

FLNEIISDFDSLLDNPKFRVITKIKTIGSTYMAASGVTPDVNTNGFASSN

KEDKSERERWQHLADLADFALAMKDTLTNINNQSENNFMLRIGMNKGGVL

AGVIGARKPHYDIWGNTVNVASRMESTGVMGNIQVVEETQVILREYGFRF

VRRGPIFVKGKGELLTFFLKGRDKLATFPNGPSVTLPHQVVDNS

Or human adenylate cyclase 3 (UniProtKB: O60266):

(SEQ ID NO: 17)
MPRNQGFSEPEYSAEYSAEYSVSLPSDPDRGVGRTHEISVRNSGSCLCLP

RFMRLTFVPESLENLYQTYFKRQRHETLLVLVVFAALFDCYVVVIVICAV

VFSSDKLASLAVAGIGLVLDIILFVLCKKGLLPDRVTRRVLPYVLWLLIT

AQIFSYLGLNFARAHAASDTVGWQVFFVFSFFITLPLSLSPIVIISVVSC

VVHTLVLGVTVAQQQQEELKGMQLLREILANVFLYLCAIAVGIMSYYMAD

RKHRKAFLEARQSLEVKMNLEEQSQQQENLMLSILPKHVADEMLKDMKKD

ESQKDQQQFNTMYMYRHENVSILFADIVGFTQLSSACSAQELVKLLNELF

ARFDKLAAKYHQLRIKILGDCYYCICGLPDYREDHAVCSILMGLAMVEAI

SYVREKTKTGVDMRVGVHTGTVLGGVLGQKRWQYDVWSTDVTVANKMEAG

GIPGRVHISQSTMDCLKGEFDVEPGDGGSRCDYLEEKGIETYLIIASKPE

VKKTATQNGLNGSALPNGAPASSKSSSPALIETKEPNGSAHSSGSTSEKP

EEQDAQADNPSFPNPRRRLRLQDLADRVVDASEDEHELNQLLNEALLERE

SAQVVKKRNTFLLSMRFMDPEMETRYSVEKEKQSGAAFSCSCVVLLCTAL

VEILIDPWLMTNYVTFMVGEILLLILTICSLAAIFPRAFPKKLVAFSTWI

DRTRWARNTWAMLAIFILVMANVVDMLSCLQYYTGPSNATAGMETEGSCL

ENPKYYNYVAVLSLIATIMLVQVSHMVKLTLMLLVAGAVATINLYAWRPV

FDEYDHKRFREHDLPMVALEQMQGFNPGLNGTDRLPLVPSKYSMTVMVFL

MMLSFYYFSRHVEKLARTLFLWKIEVHDQKERVYEMRRWNEALVTNMLPE

HVARHFLGSKKRDEELYSQTYDEIGVMFASLPNFADFYTEESINNGGIEC

LRFLNEIISDFDSLLDNPKFRVITKIKTIGSTYMAASGVTPDVNTNGFAS

SNKEDKSERERWQHLADLADFALAMKDTLTNINNQSFNNFMLRIGMNKGG

VLAGVIGARKPHYDIWGNTVNVASRMESTGVNIGNIQVVEETQVILREYG

FRFVRRGPIFVKGKGELLTFFLKGRDKLATFPNGPSVTLPHQVVDNS under the control of either the yeast GAL I or GAL10 promoters.

Biosensors with yeast cells expressing the hybrid olfactory receptor, the human Gα, Gβ, and Gγ subunits, and human adenylate cyclase are tested for expression of the components and for signal transduction by the hybrid OR.

Example 2: Using Real Time Detection to Quantitate Ligand Binding at a Repertoire of Olfactory Receptors A plurality of biosensors as described in Example 1, are used for human Olfactory Receptors from OR Family OR7. The Yeast cells with the OR7 family Olfactory Receptors are also genetically modified to include a recombinant GFP gene expressed by a control region activated by cAMP. Thus, when the biosensor is activated by an odorant, the biosensor will produce GFP and activity can be monitored by fluorescence.

Olfactory Receptors in the OR7 family are receptors for mammalian pheromones such as those related to androstenone. A panel of odorants is screened against a panel of androstenone related molecules, including, androstadienol (5,16-androstadien-3β-ol), androstadienone (androsta-4,16-dien-3-one), androstanol (5α-androst-16-en-3α-ol), and estratetraenol (estra-1,3,5(10),16-tetraen-3-ol).

Yeast cells expressing different members of the OR7 family of Olfactory Receptors are placed into separate wells or containers, interrogated with individual odorants from the panel, and fluorescence readings are made at time points 0, 10 seconds, 20 seconds, 30 seconds, 1 minute, 2 minutes, 3 minutes, 4 minutes, 5 minutes, 10 minutes, 20 minutes, 30 minutes, 40 minutes, 50 minutes, and 1 hour.

Example 3: Making a Biosensor with Human Olfactory Receptor OR1A1

The full length human olfactory receptor OR1A1 was used to make the expression plasmids NIXp218 and NIXp354. In both NIXp218 and NIXp354, the nucleic acid encoding OR1A1 is under the control of a GAL1-10 promoter. A general plasmid map for the OR constructs is shown in FIG. 1. In NIXp354, OR1A1 is fused at its N-terminal end with a FLAG tag (SEQ ID NO:1), and at its C-terminal end with the coding sequence for red fluorescent protein (RFP).

Plasmid NIXp354 or NIXp218 was placed in a haploid *Saccharomyces cerevisiae* (MATa strain). Expression of OR1A1 from NIXp354 is monitored using the FLAG tag to measure expression (using an immunoassay) and cellular localization of the OR1A1 is monitored by fluorescence from the RFP. Function of the biosensor is assessed by mating the *Saccharomyces cerevisiae* strain with NIXp218 to the complementary *Saccharomyces cerevisiae* strain (MATα) which is modified with the human G protein subunits Gα, Gβ, and Gγ, and adenylate cyclase. Mating together these two yeast strains brings the OR1A1 receptor into functional association with human G protein subunits Gα, Gβ, and Gγ, and adenylate cyclase. Function of the OR1A1 receptor can be assessed by a cAMP assay following stimulation of the OR1A1 receptor.

Example 4: Making a Biosensor with Human Olfactory Receptor OR2J2

The full length human olfactory receptor OR2J2 was used to make the expression plasmids NIXp219 and NIXp352. In both NIXp219 and NIXp352, the nucleic acid encoding OR2J2 is under the control of a GAL1-10 promoter. A plasmid map for the OR constructs is shown in FIG. 1. In NIXp352, OR2J2 is fused at its N-terminal end with a FLAG tag (SEQ ID NO:1), and at its C-terminal end with the coding sequence for red fluorescent protein (RFP).

Plasmid NIXp352 or NIXp219 was placed in haploid *Saccharomyces cerevisiae* (MATa strain). Expression of OR2J2 from NIXp352 is monitored using the FLAG tag to measure expression (using an immunoassay) and cellular localization of the OR2J2 is monitored by fluorescence from the RFP. Function of the biosensor is assessed by mating the *Saccharomyces cerevisiae* strain with NIXp219 to the complementary *Saccharomyces cerevisiae* strain (MATα) which is modified with the human G protein subunits Gα, Gβ, and Gγ, and adenylate cyclase. Mating together these two yeast strains brings the OR2J2 receptor into functional association with human G protein subunits Gα, Gβ, and Gγ, and adenylate cyclase. Function of the OR2J2 receptor can be assessed by a cAMP assay following stimulation of the OR2J2 receptor.

Example 5: Making a Biosensor with Human Olfactory Receptor OR2W1

The full length human olfactory receptor OR2W1 was used to make expression plasmids NIXp220 and NIXp351. In both NIXp220 and NIXp351, the nucleic acid encoding OR2W1 is under the control of a GAL1-10 promoter. A plasmid map for the OR constructs is shown in FIG. 1. In NIXp351, OR2W1 is fused at its N-terminal end with a FLAG tag (SEQ ID NO:1), and at its C-terminal end with the coding sequence for red fluorescent protein (RFP).

Plasmid NIXp351 or NIXp220 was placed in haploid *Saccharomyces cerevisiae* (MATa strain). Expression of OR2W1 from NIXp351 is monitored using the FLAG tag to measure expression (using an immunoassay) and cellular localization of the OR2W1 is monitored by fluorescence from the RFP. Function of the biosensor is assessed by mating the *Saccharomyces cerevisiae* strain with NIXp220 to the complementary *Saccharomyces cerevisiae* strain (MATα) which is modified with the human G protein subunits Gα, Gβ, and Gγ, and adenylate cyclase. Mating together these two yeast strains brings the OR2W1 receptor into functional association with human G protein subunits Gα, Gβ, and Gγ, and adenylate cyclase. Function of the OR2W1 receptor can be assessed by a cAMP assay following stimulation of the OR2W1 receptor.

Example 6: Making a Biosensor with Human Olfactory Receptor OR5P3

The full length human olfactory receptor OR5P3 was used to make the expression plasmids NIXp217 and NIXp353. In both NIXp217 and NIXp353, the nucleic acid encoding OR5P3 is under the control of a GAL1-10 promoter. A plasmid map for the OR constructs is shown in FIG. 1. In NIXp353, OR5P3 is fused at its N-terminal end with a FLAG tag (SEQ ID NO:1), and at its C-terminal end with the coding sequence for red fluorescent protein (RFP).

Plasmid NIXp353 or NIXp217 was placed in haploid *Saccharomyces cerevisiae* (MATa strain). Expression of OR5P3 from NIXp353 is monitored using the FLAG tag to measure expression (using an immunoassay) and cellular localization of the OR5P3 is monitored by fluorescence from the RFP. Function of the biosensor is assessed by mating the *Saccharomyces cerevisiae* strain with NIXp217 to complementary *Saccharomyces cerevisiae* strain (MATα) which is modified with the human G protein subunits Gα, Gβ, and Gγ, and adenylate cyclase. Mating together these two yeast strains brings the OR5P3 receptor into functional association with human G protein subunits Gα, Gβ, and Gγ, and adenylate cyclase. Function of the OR5P3 receptor can be assessed by a cAMP assay following stimulation of the OR5P3 receptor.

Example 7: Making a Biosensor with Human Olfactory Receptor OR6A2

The full length human olfactory receptor OR6A2 was used to make the expression plasmid NIXp239. In NIXp239 the nucleic acid encoding OR6A2 is under the control of a GAL1-10 promoter. A plasmid map for the OR construct is shown in FIG. 1.

Plasmid NIXp239 was placed in haploid *Saccharomyces cerevisiae* (MATa strain). Function of the biosensor is assessed by mating the *Saccharomyces cerevisiae* strain with NIXp239 to the complementary *Saccharomyces cerevisiae* strain (MATα) which is modified with the human G protein subunits Gα, Gβ, and Gγ, and adenylate cyclase. Mating together these two yeast strains brings the OR6A2 receptor into functional association with human G protein subunits Gα, Gβ, and Gγ, and adenylate cyclase. Function of the OR6A2 receptor can be assessed by a cAMP assay following stimulation of the OR6A2 receptor.

Example 8: Making a Cell Extract with a Biosensor

In this example the yeast cells with biosensors made from OR1A1, OR2J2, OR2W1, OR5P3, and OR6A2 from Examples 3-7 are used. Yeast cells with the Olfactory Receptor, G-proteins and adenylate cyclase are lysed with glass beads in a blender. Cell debris is removed by centrifuging the lysate at 600×g. The remaining lysate is centrifuged in an ultracentrifuge (104,300×g) to obtain the membrane fraction with the Olfactory Receptor, G-proteins and adenylate cyclase. The membrane fraction is resuspended and placed into a multiwell plate for detection of odorants.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Those skilled in the art will recognize, or be able to ascertain using no more than routine experimentation, many equivalents to the specific embodiments of the invention described herein. Such equivalents are intended to be encompassed by the following claims.

We claim:

1. A method of making an Aromagraph of a product including an odorant, comprising the steps of: obtaining a plurality of biosensors, wherein each biosensor comprises a mammalian Olfactory Receptor, a G protein subunit Gα, a G protein subunit Gβ, and a G protein subunit Gγ, and a reporter, wherein binding of the odorant to the mammalian Olfactory Receptor sends a signal through the G protein subunits resulting in a signal from the reporter, wherein at least some of the biosensors have a different mammalian Olfactory Receptor; introducing the product to the plurality of biosensors; measuring the signal from the reporter for each of the plurality of biosensors; and generating a digital representation of the reporter signal for each of the plurality of biosensors to thereby make the Aromagraph.

2. The method of claim 1, wherein the product is made of a plurality of components, and the Aromagraph is made for each component of the product.

3. The method of claim 2, wherein the Aromagraph is made for a combination of the components of the product.

4. A method of describing a product including one or more odorants, wherein the method comprises quantifying an interaction of the one or more odorants with a plurality of olfactory receptors, and wherein quantifying is accomplished using the Aromagraph made by the method of claim 1.

5. The method of claim 1, wherein the biosensor is in a host cell selected from the group consisting of an *Aspergillus*, a *Trichoderma*, a *Saccharomyces*, a *Chrysosporium*, a *Klyuveromyces*, a *Candida*, a *Pichia*, a *Debaromyces*, a *Hansenula*, a *Yarrowia*, a *Zygosaccharomyces*, a *Schizosaccharomyces*, a *Penicillium*, and a *Rhizopus*.

6. The method of claim 5, wherein the biosensor is in a membrane fraction of a host cell.

7. The method of claim 1, wherein the biosensor further comprises an adenylate cyclase and wherein a nucleic acid encoding the reporter is operably linked to a control region responsive to cAMP.

8. The method of claim 7, wherein the reporter is an optical reporter.

9. The method of claim 8, wherein the optical reporter is a fluorescent protein.

10. The method of claim 9, wherein the fluorescent reporter is a green fluorescent protein, a blue fluorescent protein, a yellow fluorescent protein, or a cyan fluorescent protein.

11. The method of claim 8, wherein the optical reporter is an enzyme or a luminescent protein.

12. The method of claim 1, wherein the biosensor comprises a membrane fraction of a host cell.

13. The method of claim 1, wherein the product is in the gaseous phase.

14. The method of claim 4, wherein the product is made of a plurality of components, and the Aromagraph is made for each component of the product.

15. The method of claim 4, wherein the product is made of a plurality of components, and the Aromagraph is made for a combination of the components of the product.

* * * * *